United States Patent [19]
Klionsky et al.

[11] Patent Number: 5,559,010
[45] Date of Patent: Sep. 24, 1996

[54] NUTRIENT REGULATED GENE EXPRESSION SYSTEMS

[75] Inventors: Daniel J. Klionsky, Davis, Calif.; Monika Destruelle; Helmut Holzer, both of Freiburg, Germany

[73] Assignee: The Regents of the University of California, Oakland, Calif.

[21] Appl. No.: 222,289

[22] Filed: Apr. 4, 1994

[51] Int. Cl.$^6$ .............. C12N 1/15; C12N 15/11; C12N 15/81; C12P 21/06

[52] U.S. Cl. .............. 435/69.1; 435/254.2; 435/320.1; 536/24.1

[58] Field of Search .............. 435/69.1, 254.1, 435/254.11, 254.2, 254.21, 320.1, 240.1, 240.2; 536/23.1, 24.1, 23.74

[56] References Cited

PUBLICATIONS

Law and Segall, "The SPS100 Gene of *Saccharomyces cerevisiae* Is Activated Late in the Sporulation Process and Contributes to Spore Wall Maturation", *Mol. and Cell. Biol.* 8(2):912–922 (1988).

Mittenbühler and Holzer, "Characterization of Different Forms of Yeast Acid Trehalase in the Secretory Pathway", *Arch. Microbiol.* 155:217–220 (1991).

Mittenbühler and Holzer, "Purification and Characterization of Acid Trehalase from the Yeast suc2 Mutuant", *J. of Biol. Chem.* 263(17):8537–8543 (1988).

Fincham, *Microbiological Reviews*, Mar. 1989, pp. 148–170.

Latchman, *Eukaryotic Transcription Factors*, Mar. 30, 1992, Academic Press Inc., San Diego CA, pp. 87–89.

Destruelle et al, *Molecular and Cellular Biology*, Mar. 25, 1994, pp. 2740–2754.

*Primary Examiner*—George C. Elliott
*Assistant Examiner*—Terry A. McKelvey
*Attorney, Agent, or Firm*—Richard Aron Osman

[57] ABSTRACT

The invention provides methods and compositions for expressing a recombinant gene in eukaryotic cells, especially fungi, preferably yeast. The invention provides transcriptional regulating elements having a novel nucleotide sequence which are capable of trancriptionally regulating the expression of a cis joined gene, typically in response to the availability of certain nutrients to the host cell. Preferred regulatory elements are responsive to nutrient depletion, particulary glucose, ethanol, phosphate or a nitrogen source. Nucleic acid constructs comprising such regulatory elements operably linked to recombinant genes, cells comprising such regulatory elements, and methods of producing recombinant protein in such cells are also provided. The invention discloses regulatory elements which are induced through the ras gene product. Accordingly, the disclosed expression systems also provide a convenient marker for ras gene function. Finally, the invention also provides methods and compositions for the diagnosis and treatment of fungal infection. In particular, the invention provides gp37-derived peptides encoded by YGP1 and gp37- selective binding agents, such as antibodies.

10 Claims, 16 Drawing Sheets

Figure 1A

```
         -360        350       -340       -330       -320       -310
    ATTCGTACTC TATTGCATCT TCAAAGTCCG AAGAATCTCA GTAGGGAGTG AAGCCGGCTT

-300       -290       -280       -270       -260       -250
    CTCGATGCTA CACTTCTCGA TGCTACAGTT CAACATCGAT ACTTTGAAGA AAGAAAGCGC

-240       -230       -220       -210       -200       -190
    CTATTATATC TCTTTTACCC TATTAGTAAT AATTAGGAAA AAGGGAGAAA AAAGTACCTC

-180       -170       -160       -150       -140       -130
    ACTAAAAAAA CCATCATCTC TGAAATATAA AAAGCTTGAT AGAGGGTGAC ATTTGCTAGA

-120       -110       -100        -90        -80        -70
    ACTTCTGCTG TGTTCTCTTG GGTTATTGCT CTTATTGAAT ATCCCTTCTA TTTCTTTCTT

-60        -50        -40        -30        -20        -10
    GCTTGTAAAA AATCAGCTCA AAAACATCT ACAGGATTAA TCGTCAGTTA AGTAATACAG

TAATAGAAA
```

```
ATG AAG TTC CAA GTT GTT TTA TCT GCC CTT TTG GCA TGT TCA TCT GCC GTC
Met Lys Phe Gln Val Val Leu Ser Ala Leu Leu Ala Cys Ser Ser Ala Val

GTC GCA AGC CCA ATC GAA AAC CTA TTC AAA TAC AGG GCT GTT AAG GCA TCT
Val Ala Ser Pro Ile Glu Asn Leu Phe Lys Tyr Arg Ala Val Lys Ala Ser

CAC AGT AAG AAT ATC AAC TCC ACT TTG CCG GCA TGG GAT GGG TCT AAC TCT
His Ser Lys Asn Ile Asn Ser Thr Leu Pro Ala Trp Asp Gly Ser Asn Ser

AGC AAT GTT ACC TAC GCT AAT GGA ACA AAC AGT ACT ACC AAT ACT ACT ACT
Ser Asn Val Thr Tyr Ala Asn Gly Thr Asn Ser Thr Thr Asn Thr Thr Thr

GCC GAA AGC AGT CAA TTA CAA ATC ATT GTA AGA GGT GGT CAA GTA CCA ATC
Ala Glu Ser Ser Gln Leu Gln Ile Ile Val Arg Gly Gly Gln Val Pro Ile

ACC AAC AGT TCT TTG ACC CAC ACA AAC TAC ACC AGA TTA TTC AAC AGT TCT
Thr Asn Ser Ser Leu Thr His Thr Asn Tyr Thr Arg Leu Phe Asn Ser Ser

TCT GCT TTG AAC ATT ACC GAA TTG TAC AAT GTT GCC CGT GTT GTT AAC GAA
Ser Ala Leu Asn Ile Thr Glu Leu Tyr Asn Val Ala Arg Val Val Asn Glu

ACG ATC CAA GAT AAG TCA TCC GCC GGT GCC GTT GTT GTT GCC AAC GCC AAA
Thr Ile Gln Asp Lys Ser Ser Ala Gly Ala Val Val Val Ala Asn Ala Lys

TCT TTG GAA GCT GTC TCA TTC TTC TTC TCT ATC ATT TTT GAC ACC GAA AAG
Ser Leu Glu Ala Val Ser Phe Phe Phe Ser Ile Ile Phe Asp Thr Glu Lys

CCT ATT GTT GTC ACT GAA GAT TCC GCT TAT GCC ATT CCA GTC GCT AAC AAT
Pro Ile Val Val Thr Glu Asp Ser Ala Tyr Ala Ile Pro Val Ala Asn Asn

AAG AAC GCT ACC AAA CGT GGT GTC TTG TCC GTC ACT TCT GAC AAA TTA GTG
Lys Asn Ala Thr Lys Arg Gly Val Leu Ser Val Thr Ser Asp Lys Leu Val

TAC TCC GGT GTC TTC ACT CCA CCT ACT GCT TGT TCT TAC GGT GCT GGT TTG
Tyr Ser Gly Val Phe Thr Pro Pro Thr Ala Cys Ser Tyr Gly Ala Gly Leu
```

Figure 1B

```
CCT GTT GCT ATC GTT GAT GAC CAA GAC GAA GTT AAA TGG TTC TTC GAT GCT
Pro Val Ala Ile Val Asp Asp Gln Asp Glu Val Lys Trp Phe Phe Asp Ala

TCT AAG CCA ACT TTA ATC TCT TCT GAC TCG ATT ATC AGA AAG GAA TAC AGT
Ser Lys Pro Trp Leu Ile Ser Ser Asp Ser Ile Ile Arg Lys Glu Tyr Ser

AAC TTC ACT ACT CCT TAT GGT CTA TTA GAA AAC GGT GTT CCA ATT GTT CCA
Asn Phe Thr Thr Pro Tyr Gly Leu Leu Glu Asn Gly Val Pro Ile Val Pro

ATT GTC TAT GAC GGT GGT TAC TCT TCC AGT TTG ATT GAC TCC TTG AGT TCT
Ile Val Tyr Asp Gly Gly Tyr Ser Ser Ser Leu Ile Asp Ser Leu Ser Ser

GCC GTT CAA GGT TTG GTT GTT GTT TCT TCT GGT TCT ACC AAC TCA ACC TCA
Ala Val Gln Gly Leu Val Val Val Ser Ser Gly Ser Thr Asn Ser Thr Ser

TCT ACT ATT GAA AGC ACT GAA ATC CCA GTC GTA TAT GCT CAA GCT AAC ACT
Ser Thr Ile Glu Ser Thr Glu Ile Pro Val Val Tyr Ala Gln Ala Asn Thr

CCA TTA AAC TTT ATT GAC AAC AAA GAT GTT CCA AAG AAC GCT GTG GGT GCT
Pro Leu Asn Phe Ile Asp Asn Lys Asp Val Pro Lys Asn Ala Val Gly Ala

GGT TAC CTA TCC CCA ATT AAG GCC CAA ATC TTG TTG TCC ATT GCT GCC GTT
Gly Tyr Leu Ser Pro Ile Lys Ala Gln Ile Leu Leu Ser Ile Ala Ala Val

AAT GGT GTC ACC TCC AAG TCC GCT CTG GAA AGC ATT TTC CCA TGA ACT GAT
Asn Gly Val Thr Ser Lys Ser Ala Leu Glu Ser Ile Phe Pro ***
```

AGATATTAAA TCTAGCGAAG CATAGAGATT CTTTTTTTAC CAGTCATCAT AACCATTATT

TTACAAAATT TCCACGCAAC AGCTTTTATT TTCGTTCGTA ATAGGAACCA TACTTCCCAT

TAAAGCAGTA TGATTGTTTT ATACACCTTT TTATTGTTAT TTAAGACATA CCCCAAATAA

TTAATTAATT AATTGATGAA AGAATCATAT AAATTCTTGG CCATACATAT TTTTTTATTA

TCTTTTGCTA CATTGACCAT AGGTGAATAT CTTCCCGGGG TGACACTCCA CTGAAGTGGG

AAAAAAAGAA AAGTTTTAAA ACATTGCTCA CCTTAAGTCT CGAAGGTCTA GCATTCACTA

CCTGTAAGTG TCAAGACCCC ACAGGTATAC ATGATACAAT AAAGAAACAA TGTCCGTATA

ATTGTATACA TTTTACTACA GATAAGGGAT CTCACCCCCT TCTTTTGTGT CTAAGTGAAA

TCTTCTGATA TATTTAGTGT TTTATAGCGT CCATGTTTTA AACTAGAACG GCAAAATAGT

AGTTGTTGTA AACGCTTATT TTCGAGACAT CAGGTAAAAA GATAGTTAAA TCTTACAATC

AATGCATGTA GTGAGTGGCG TTTATCAATA GTTTTTAACA ATTCCCATTT TGAAAGAAGC

CCACAACAAC CCTAGTAGTT CGTTATATAC GTTATGATGG TCAAGTGTCA CAGTACGGAA

AGCTT

| Percent glucose | [Asn]$_i$ | Invertase activity |
|---|---|---|
| —△— | 0.002% | —▲— |
| —○— | 0.02% | —●— |
| —□— | 0.2% | —■— |

NUTRIENT REGULATED GENE EXPRESSION SYSTEMS

The research carried out in the subject application was supported in part by grants from the National Institutes of Health. The government may have rights in any patent issuing on this application.

TECHNICAL FIELD

The technical field of this invention concerns eukaryotic gene expression systems.

BACKGROUND

Fungi and yeast in particular provide useful systems for the production of many gene products, especially proteins, that have pharmacological, cosmetic, agricultural, industrial, or other commercial uses. Heterologous proteins may be synthesized, post-translationally modified, folded, and secreted in the context of a eukaryotic host.

Recombinant genes are typically placed under the transcriptional control of heterologous gene regulatory elements. Such elements are generally selected to provide high levels of gene expression, whether constitutive or inducible/repressible. However, constitutive gene expression provides neither controlled expression, temporally or otherwise, nor means for differentially expressing the recombinant protein of interest relative to undesired background gene expression.

Unfortunately, presently available regulated expression systems provide either inferior expression or limit host cells or expression conditions. For example, the strongest glycolytic promoters are induced upon the addition of glucose. Glucose however, favors the synthesis of most cellular proteins so these promoters do not permit differential expression of the target protein. Some phosphate-regulated promoters are available, but these are relatively weak promoters. Galactose-regulated promoters require that the culture be grown in galactose; a nutrient that will not sustain the growth of many yeast strains.

What is needed is a strong, inducible eukaryotic gene expression system, broadly adaptable to conventional expression hosts and capable of differentially expressing the target protein.

RELEVANT LITERATURE

The purification and characterization of an acid trehalase activity is described in Mittenbühler and Holzer (1988 and 199 1) J. Biol. Chem. 263:8537–8543 and Arch. Microbiol. 155:217–220, respectively.

A sporulation-specific gene with some sequence homology to YGP1 is described in Law and Segall (1988) Mol. Cell. Biol. 8: 912–922.

SUMMARY OF THE INVENTION

The invention provides methods and compositions for expressing a recombinant gene in eukaryotic cells, especially fungi, preferably yeast. Recombinant production of any gene product almost invariably involves isolating and purifying the product from the host or spent media. Depending on the particular product and host, these steps often comprise the bulk of production time, labor and material expense. The disclosed methods and compositions provide high levels of expression of a target recombinant gene against a low background gene expression. Accordingly, the disclosed expression systems provide lower product isolation and purification costs than prior art systems.

The invention provides transcriptional regulating elements having a novel nucleotide sequence which are capable of trancriptionally regulating the expression of a cis joined gene, typically in response to the availability of certain nutrients to the host cell. Preferred regulatory elements are responsive to nutrient depletion, particularly glucose, ethanol, phosphate or a nitrogen source. Nucleic acid constructs comprising such regulatory elements operably linked to recombinant genes, cells comprising such regulatory elements, and methods of producing recombinant protein in such cells are also provided.

The invention discloses regulatory elements which are induced through the ras gene product. Accordingly, the disclosed expression systems also provide a convenient marker for ras gene function. Finally, the invention also provides methods and compositions for the diagnosis and treatment of fungal infection. In particular, the invention provides gp37-derived peptides encoded by YGP1 and gp37- selective binding agents, such as antibodies.

BRIEF DESCRIPTION OF THE FIGURES

FIG. 1. Nucleotide sequence of the non-transcribed strand of the YGP1 gene (SEQ ID NO:1). The nucleotide sequence was obtained for both strands of YGP1 by the method of Sanger et al (46) on two subclones in the vector pTZ18R. Two putative transcription initiation sequences (TATA boxes) in the 5' untranslated region are double-underlined and the putative 3' polyadenylation signal is underlined and italicized. Nucleotide 1 corresponds to the first nucleotide of the initiation codon. Translation of the predicted open reading frame of the YGP1 gene (SEQ ID NO:2) is shown below the nucleic acid sequence. Amino acid 1 corresponds to the first amino acid of precursor gp37. Potential sites for asparagine-linked glycosylation are indicated in bold letters. The amino acid sequences derived from protein sequencing are underlined and sequences used for the design of oligonucleotide primers are underlined and italicized.

DESCRIPTION OF SPECIFIC EMBODIMENTS

Figure 2A:
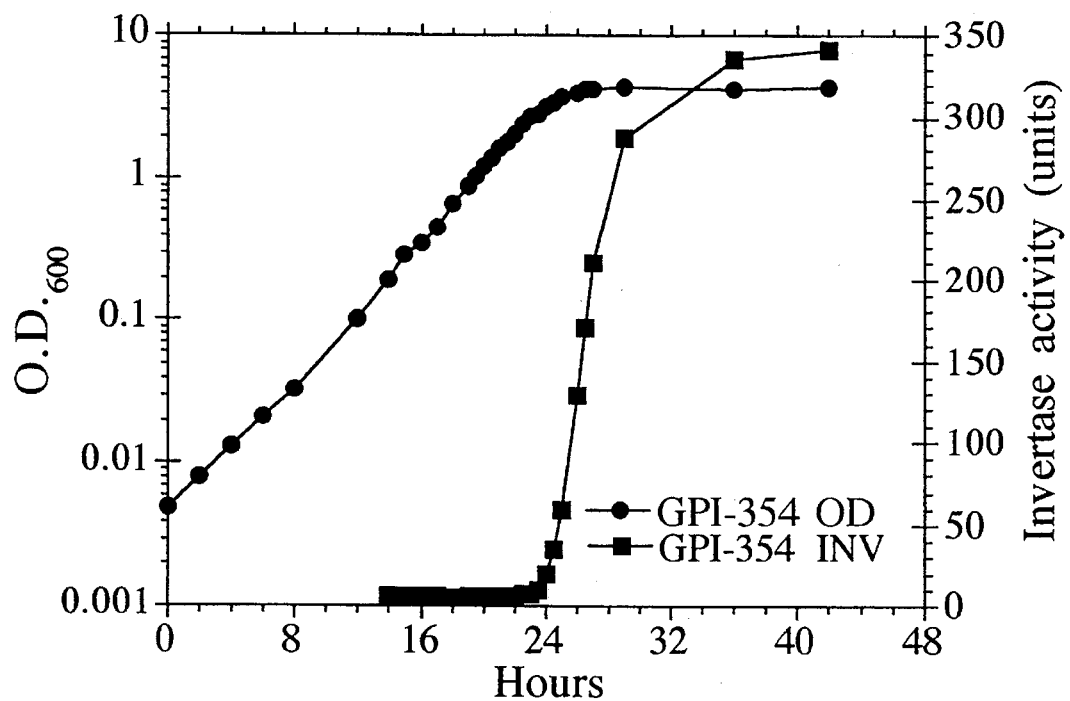
FIGS. 2(A)–(F). Expression of invertase activity from YGP1-SUC2 gene fusion constructs compared to O.D.$_{600}$ and glucose concentration. (A) O.D.$_{600}$ and (B) glucose concentration versus invertase activity for strain SEY2108 transformed with a plasmid encoding GPI-354 (SEY2108/GPI-354). Essentially identical results were obtained with the GPI-39 hybrid protein. (C) O.D.$_{600}$ versus invertase acitivty for strain SEY2108/API-191. Utilization of glucose in this experiment was essentially identical to that shown in panel B. (D) O.D.$_{600}$ versus invertase activity for strain SEY6210/GPI-354. Two cultures were grown in parallel. At the 28.5 hr time point of growth, cycloheximide (CHX; 100 mg/ml final concentration) in ethanol (0.5% final concentration) or only ethanol were added to each culture. (E) O.D.$_{600}$ and (F) glucose concentration versus invertase activity for strain SEY6210/GPI-354. Two cultures were grown in parallel. One culture, was grown in YNB medium containing 2% glucose and supplemented with auxotrophic amino acids as needed. The other culture was grown in YNB medium containing 3% glucose and supplemented with auxotrophic amino acids as needed with the exception that histidine was added at ~0.4X (0.0008%) the normal concentration.

The invention discloses novel gene regulatory elements, genetic constructs, gene expression systems and methods for producing recombinant proteins. The novel gene expression regulatory elements are nucleic acids comprising a portion of SEQ ID NO:1 capable of regulating the transcription of a cis-joined gene.

The subject nucleic acids are either isolated, partially purified, or recombinant. An "isolated" nucleic acid is present as other than a naturally occurring chromosome or transcript in its natural state and isolated from (not joined in sequence to) at least one nucleotide with which it is normally assocated on a natural chromosome; a partially pure nucleic acid constitutes at least about 5%, preferably at least about 30%, and more preferably at least about 90% by weight of total nucleic acid present in a given fraction; and a recombinant nucleic acid is flanked—joined in sequence on at least one side—by at least one nucleotide with which it is not normally associated on a natural chromosome.

The subject nucleic acids comprise unique portions of SEQ ID NO:1. Unique portions of the disclosed nucleic acid are of length sufficient to distinguish previously known nucleic acids. Thus, a unique portion has a nucleotide sequence at least long enough to define a novel oligonucleotide, usually at least about 15 or 18 bp, preferably at least about 24 bp, more preferably at least about 36 bp in length. A unique portion is frequently joined in sequence to other nucleotides which may be nucleotides which naturally flank the unique portions.

The invention also provides polynucleotides of at least about 20 bp, preferably at least about 60, more preferably at least about 180 bp, sharing substantial sequence similarity with a similar size portion of SEQ ID NO:1. Substantially similar sequences hybridize under low stringency conditions, for example, at 50° C. and SSC (0.9 M saline/0.09 M sodium citrate) and remain bound when subject to washing at 55° C. with SSC. Regions of non-identity of substantially similar polynucleotides preferably encode redundant codons.

The invention also provides for the disclosed nucleic acids modified by transitions, transversions, deletions, insertions, substitutions or other modifications and also provides for flanking sequences; included are DNA and RNA sequences, sense and antisense. The nucleic acids can be subject to purification, synthesis, modification, sequencing, recombination, incorporation into a variety of vectors and host cells, expression, transfection, administration or methods of use disclosed in standard manuals such as Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, New York, N.Y., 1992) or that are otherwise known in the art. See also, Romanos et al. (1992) Yeast 8, p. 423–488, and references therein.

Preferred host cells are yeast, particularly Pichia Pastons, Hansenula polymorpha, Kluyveromyces lactis, Yarrowia lipolytica and Schezosuccharomiyces pombe. Preferred expression systems involve a chemostat capable of maintaining a low steady state level of a specific nutrient, see below. Generally, regulatory sequences from YGP1 (SEQ ID NO:1) are placed into a plasmid vector that has a multiple cloning site (MCS) and is capable of being maintained in both yeast and E. coli. The MCS may be constructed in all three reading frames. The gene encoding a protein of interest is cloned into the MCS behind the promotoer and then is subject to regulation by the YGP1 control elements. All recombinant manipulations may be done in E. coli. The final plasmid construct is then introduced in to yeast. Cultures are grown to a high density in medium containing non-limiting nutrients. One or more nutrients are then limited and the gene becomes highly expressed. It may be advantageous to include a signal sequence and signal sequence cleavage sites in the plasmid vector 5' of the MCS.

The present invention also discloses methods and compositions useful for the treatment and/or diagnosis of fungal infection. The compositions include peptides comprising unique portions of the disclosed gp37 (SEQ ID NO:2). A "unique portion" has an amino acid sequence unique to that disclosed in that it is not found in any previously known protein and has a length at least long enough to define a novel peptide. Unique portions are found to vary from about 5 to about 25 residues, preferably from 5 to 10 residues in length, depending on the particular amino acid sequence and are readily identified by comparing the subject portion sequences with known peptide/protein sequence data bases. Preferred unique portions include residues critical for fungal pathogenesis, which residues are readily identified by correlating deletion or substitution mutants with pathogenesis.

The subject peptides may be free or covalently coupled to other atoms or molecules. Frequently the peptides are present as a portion of a larger polypeptide comprising the subject peptide where the remainder of the polypeptide need not be gp37-derived. The invention also provides polypeptides of at least about 40 residues, preferably at least about 80, more preferably at least about 160 residues, sharing substantial sequence similarity with a similar size portion of SEQ ID NO:2. A "substantially full-length" gp37 comprises at least about 300 amino acids of the disclosed polypeptide sequence. "Substantially similar" sequences share at least about 60%, more preferably at least about 80%, and most preferably at least about 90% sequence identity. Where the sequences diverge, the differences are generally point insertions/deletions or conservative substitutions, i.e. a cysteine/threonine or serine substitution, an acidic/acidic or hydrophobic/hydrophobic amino acid substitution, etc.

The subject poly/peptides are "isolated", meaning unaccompanied by at least some of the material with which they are associated in their natural state. Generally, an isolated poly/peptide constitutes at least about 1%, preferably at least about 10%, and more preferably at least about 50% by weight of the total poly/peptide in a given sample. By pure peptide/polypeptide is intended at least about 60%, preferably at least 80%, and more preferably at least about 90% by weight of total poly/peptide. Included in the subject poly/peptide weight are any atoms, molecules, groups, etc. covalently coupled to the subject poly/peptides, such as detectable labels, glycosylations, phosphorylations, etc.

The subject poly/peptides may be isolated or purified in a variety of ways known to those skilled in the art depending on what other components are present in the sample and to what, if anything, the poly/peptide is covalently linked. Purification methods include electrophoretic, molecular, immunological and chromatographic techniques, especially affinity chromatography and RP-HPLC in the case of peptides. For general guidance in suitable purification techniques, see Scopes, R., Protein Purification, Springer-Verlag, N.Y. (1982).

Binding agents specific for gp37 are produced or identified by a variety of ways. For example, gp37 peptides are used as immunogens to generate specific polyclonal or monoclonal antibodies. See, Harlow and Lane (1988) Antibodies, A Laboratory Manual, Cold Spring Harbor Laboratory, for general methods. Other prospective gp37-peptide specific agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. See, e.g. Houghten et al. and Lam et al (1991) Nature 354, 84 and 81, respectively and Blake and Litzi-Davis (1992), Bioconjugate Chem 3, 510.

Useful agents are identified with assays employing a compound comprising the subject poly/peptides or encoding nucleic acids. A wide variety of in vitro, cell-free binding assays, especially assays for specific binding to immobilized compounds comprising a gp37 poly/peptide find convenient use. See, e.g. Fodor et al (1991) Science 251, 767 for the light directed parallel synthesis method. Such assays are amenable to scale-up, high throughput usage suitable for volume drug screening.

Useful agents are typically those that bind to gp37 and selectivley inhibit pathogenesis. Generally, selective binding requires a binding affinity of $10^{-6}$M, preferably $10^{-8}$M, more preferably $10^{-10}$M, under in vitro conditions. Useful agents may be found within numerous chemical classes, though typically they are organic compounds; preferably small organic compounds. Small organic compounds have a molecular weight of more than 150 yet less than about 4,500, preferably less than about 1500, more preferably, less than about 500. Exemplary classes include peptides, saccharides, steroids, heterocyclics, polycyclics, substituted aromatic compounds, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways, e.g. to enhance their proteolytic stability. Other methods of stabilization may include encapsulation, for example, in liposomes, etc.

For therapeutic uses, the compositions and agents disclosed herein may be administered by any convenient way. Small organics are preferably administered orally; other compositions and agents are preferably administered parenterally, conveniently in a pharmaceutically or physiologically acceptable carrier, e.g., phosphate buffered saline, or the like. Typically, the compositions are provided topically or added to a retained physiological fluid such as blood. Generally, the amount administered will be empirically determined, typically in the range of about 10 to 1000 μg/kg of the recipient. For peptide agents, the concentration will generally be in the range of about 50 to 500 μg/ml in the dose administered. Other additives may be included, such as stabilizers, bactericides, etc. These additives will be present in conventional amounts.

The following examples are offered by way of illustration and not by way of limitation.

EXAMPLES

In the yeast *Saccharomyces cerevisiae*, a major regulation of cell division occurs in the $G_1$ phase (41). At this point in the cycle, the cell must sense and coordinate both intracellular and extracellular signals before committing to a subsequent round of growth. Upon completion of the cell cycle, cells in a heterothallic haploid culture have two options; they can begin a new round of division or they can enter stationary phase. When nutrients are limiting, cells exit the division cycle and enter into stationary phase. The exact timing of entry into stationary phase and the resulting physiological responses are not well understood.

Yeast cells undergo various physiological changes in response to nutrient depletion (32, 40, 53). Two changes that have been well documented are strengthening of the cell wall and accumulation of trehalose (8, 9, 47, 50). In general, different phases of the growth cycle are marked by major alterations in gene expression. As cells enter stationary phase the transcription of most genes and the level of mRNA decreases (53). Similarly, there is a substantial drop in overall protein synthesis (4). In contrast, some genes are expressed at higher levels during or after the diauxic shift following respiro-fermentative (logarithmic) growth and in certain cases, the gene products appear to be required for survival under stress conditions (16, 45, 53). Expression of genes that are involved in various stress responses appears to be controlled through Ras-regulated cAMP-dependent protein kinase and the Snf1p protein kinase signal transduction pathways (53).

Acid trehalase is one of the enzymes that is derepressed in stationary phase (i.e., post-glucose exhaustion) cells (18). Previously, a protein preparation reportedly containing 7000-fold purifiied acid trehalase activity was used to generate antisera (36). The biosynthesis of a highly glycosylated yeast protein that was reported to be the vacuolar trehalase was analyzed in sec mutants (37).

To continue analysis of the synthesis and regulation of acid trehalase, we decided to clone the structural gene relying on published data obtained from the purification of the enzyme. In this report, we show that the purified protein preparation having high acid trehalase activity copurified with an additional protein, and that this highly glycosylated additional protein does not exhibit acid trehalase activity, but is actually a secretory protein which we call gp37. This protein is the product of a novel yeast gene, YGP1. We have cloned and sequenced the YGP1 gene and examined the regulation of its expression. We have found that YGP1-specific mRNA and the corresponding protein product are present at low levels during respiro-fermentative (logarithmic) growth. Both increase substantially in response to limitation of several central nutrients. These results show that YGP1 is regulated through a complex mechanism that senses and responds to multiple environmental signals and that the gene product plays a role in cellular adaptations prior to entry into stationary phase.

MATERIALS AND METHODS

Strains and media. *Escherichia coli* strains used in this study were MC1061 F⁻ hsdR hsdM⁺ araD139 Δ(araABOIC-leu)7679 Dlac$_c$74 galU galK rpsL (5) and ΔH5a F⁻ f80dlacZΔM15 Δ(lacZYA-argF)U169 deoR recA1 endA1 hsdR17 supE44 1⁻ thi-1 gyrA96 relA1. Yeast strains used were SEY2108 MATa ura3-52 leu2-3,112 suc2Δ9 Δprc1::LEU2 (2), SEY6211 MATa ura3-52 leu2-3,112 his3-Δ200 trpl-Δ901 ade 2-101 suc2Δ9 and SEY6210 MATa ura3-52 leu2-3,112 his3-Δ200 trpl-Δ901 lys2-801suc2Δ9 (42). Standard methods were used to construct yeast strains DKY9001 MATa ura3-52 leu2-3,112 his3-Δ200 trpl-Δ901 lys2-801suc2Δ9 Δsnf1::LEU2, MDY1 MATa ura3-52 leu2-3,112 his3-Δ200 trpl -Δ901 lys 2 -801suc2Δ9 Dygp1::URA3 and MΔY2 MATa ura3-52 leu2-3,112 his3 -D200 trpl-Δ901 ade2-101 suc2Δ9 Δygp1::URA3. The plasmid pJH80, Dsnf1::LEU2 was used to disrupt the SNF1 gene (21 ).

Standard yeast (48, 54) and *E. coli* (35) media were used and supplemented as needed. The nomenclature of Lewis (31) was used to describe growth phases of the yeast cultures. Specifically, the term "respiro-fermentative" refers to the initial logarithmic phase of growth primarily characterized by fermentation of glucose. The word "logarithmic" is included in parentheses throughout the text as a reminder. For specific growth experiments with limiting nutrients, the following media were used: A) For limiting carbon and energy source, cells were grown in synthetic minimal medium. This consisted of 0.7% yeast nitrogen base (YNB), amino acids as necessary, vitamins and 2% glucose. To test for growth on non-fermentable carbon sources, the glucose was reduced to 0.05% and the medium was suplemented with B) 3% glycerol/lactate, C) 2% pyruvate or D) 2% ethanol. E) To analyze expression due to limiting phosphate, cells were grown in 50 mM 2-(N-morpholino)ethanesulfonic acid, pH 5.5, 1% asparagine, 10 mM MgSO$_4$, 27 mM KCl, 4.5% glucose, vitamins, trace elements including 0.002 mM FeCl$_3$, and 0.002–2 mM potassium phosphate. F) For limiting sulfate, cells were grown in 7.3 mM potassium phosphate, 1.7 mM NaCl, 4.1 mM MgCl$_2$, vitamins, trace elements, 2% asparagine, 4.5% glucose and 0.001–10 mM MgSO$_4$. G) For experiments with limiting nitrogen, the medium consisted of 7.3 mM potassium phosphate, 1.7 mM NaCl, 4.1 mM MgCl$_2$, 10 mM MgSO$_4$, vitamins, trace elements, 5% glucose and 0.002–0.2% asparagine.

Reagents. YNB, Bacto-tryptone, Bacto-peptone, Bacto-yeast extract and Bacto-agar were from Difco Laboratories (Detroit, Mich.). DNA restriction and modifying enzymes were from New England Biolabs, Inc. (Beverly, Mass.) and Boehringer Mannheim Biochemicals (Indianapolis, Ind.). Zymolyase 100 T was purchased from ICN Biomedicals (Irvine, Calif.), oxalyticase was obtained from Enzogenetics (Corvallis, Oreg.), endoproteinase Lys-C from Boehringer Mannheim Biochemicals (Mannheim, Germany) and endoglycosidase H was from Boehringer Mannheim Biochemicals (Indianapolis, Ind.). Hybond N⁺ membranes for Southern and Northern blots, [a-$^{32}$P]dCTP (3,000 Ci/mmol) and [$^{35}$S]dATPaS (>1,000 Ci/mmol) were from Amersham Buchler (Braunschweig, Germany). Polyvinyl difluoride membranes for Western blots (Immobilon-P) were from Millipore (Bedford, Mass.). Goat anti-rabbit antibodies were purchased from Bio-Rad Laboratories (Hercules, Calif.) and the ECL chemiluminescent detection kit was from Amersham (Arlington Heights, Ill.). Sequenase 2.0 and random priming kits were from United States Biochemical Corp. (Cleveland, Ohio). All other chemicals were from Sigma Chemical Co. (St. Louis, Mo.).

Purification of acid trehalase/gp37, proteinase digestion and peptide sequencing.

Purification of acid trehalase/gp37 was carried out as previously described (36). A portion (100 μg) of the purified preparation was deglycosylated with endoglycosidase H as described below. Half of the deglycosylated protein was digested with endoproteinase Lys-C which cleaves on the carboxyl side of lysine residues, and used to determine the sequence of internal peptide fragments by the Edman degradation method. The remaining portion was also subjected to Edman degradation to determine the amino-terminal sequence of the mature protein.

Cloning, sequencing and DNA analysis of YGP1. Peptide sequences from the amino terminus and an internal peptide of the acid trehalase/gp37 protein were used as the basis for synthesizing degenerate oligonucleotides (7). The oligonucleotides were used in a polymerase chain reaction (PCR) with yeast genomic DNA isolated from strain SEY6210. A specific 0.5 kb DNA fragment was amplified and recovered. This fragment was labeled with [$^{32}$P]dCTP by the random priming method (14) and used to screen a YCp50-based genomic DNA library (43) by colony hybridization (44). Four plasmids were detected that hybridized with the probe. These plasmids contained a common 1.9 kb HindIII restriction enzyme fragment. This fragment was subcloned into the vector pTZ18R (Pharmacia, Freiburg) to construct the plasmid pTZYGP1. The nucleotide sequence of both strands of the 1.9 kb fragment containing the YGP1 gene was determined by the dideoxy chain termination method (46).

Genomic and plasmid DNA from *Saccharomyces cerevisiae* and plasmid DNA from *Escherichia coli* were prepared as described previously (3, 48). Standard procedures were followed for subcloning DNA fragments and for identifying recombinant clones (44). Southern blot analysis (49) utilized radiolabeled DNA hybridization probes prepared by the random priming method as described above. The DNA was separated on a 0.8% agarose gel, incubated in 0.25 M HCl and blotted onto a Hybond N$^+$ membrane in 0.4 M NaOH.

Disruption of YGP1. The plasmid pTZYGP1 contains a unique HpaI site within the YGP1 structural gene. A 1.1 kb HindIII fragment containing the URA3 gene was isolated from plasmid YEp24 and the overhanging 5' ends filled in by treatment with the Klenow fragment of DNA polymerase I. The blunt-ended URA3 fragment was cloned into the HpaI site of pTZYGP1 to generate the plasmid pTZYGP1.1. The HindIII fragment of pTZYGP1.1 containing the YGP1 gene disrupted with URA3 was isolated and used to transform yeast strains SEY6210 and SEY6211 using approximately 10 μg of DNA (22). Ura$^+$ colonies were isolated and examined by Southern blot to confirm the site of integration. Yeast strains MDY1 and MDY2 contained the URA3 gene integrated at the chromosomal YGP1 locus.

RNA isolation and Northern blot analysis. Total RNA was isolated from respiro-fermentative (logarithmic) and respiratory phase cultures (31) of yeast strain SEY6210. The RNA was prepared by the method of Chirgwin et al (6). For Northern blot analysis, 10 mg of total RNA was separated on a 1.0% formaldehyde agarose gel. Following electrophoresis, the RNA was transferred to a Hybond N$^+$ membrane in 0.04 M NaOH. YGP1-specific RNA was detected by hybridization with the radiolabeled 0.5 kb fragment derived from PCR as described above.

Antibodies. To produce antisera to gp37, a synthetic peptide was synthesized (Multiple Peptide Systems, San Diego, Calif.) based on the amino acid sequence of one of the endoproteinase Lys-C fragments from the acid trehalase/gp37 protein preparation. The peptide corresponded to amino acid residues 102–116 of the precursor protein and was conjugated at the amino terminus to keyhole limpet hemocyanin. Standard procedures were used to generate antiserum in New Zealand White Rabbits.

Western blot analysis. Yeast cultures were grown in YPD medium for approximately 48 hours to exhaust the glucose. Total yeast protein was extracted by vigorous agitation in the presence of glass beads in 0.1 M sodium acetate, pH 5.2 and total protein concentrations were determined by the methods of Lowry (34). A portion of protein from each time point (0.25 mg) was denatured by heating at 95° C. for 5 min in 0.27 M sodium acetate, pH 5.2, 0.5% SDS, 0.5% b-mercaptoethanol. Where indicated, protein was deglycosylated by denaturation at 95° C. for 5 min in 0.27 M sodium acetate, pH 5.2, 0.5% SDS, 0.5% b-mercaptoethanol followed by treatment with endoglycosidase H (20 mU) for 48 hours at 37° C. An aliquot of the crude extract or deglycosylated protein (35–50 μg) was loaded onto a 10% polyacrylamide SDS gel. Following electrophoresis, the proteins were transferred to a polyvinyl difluoride membrane by electroblotting. The filters were blocked and incubated for 14 hrs with a 1:20,000 dilution of antibody to gp37. Antibody binding was visualized by subsequent incubation with horseradish peroxidase-conjugated goat anti-rabbit antibody and the ECL detection reagents followed by chemiluminescent exposure of x-ray film.

Hybrid protein construction. SalI restriction enzyme sites were placed after amino acid residues 39 or 354 of precursor gp37 by PCR. An EcoRI restriction enzyme site was placed in the 5' non-coding region at nucleotide position −353 to −348 by PCR. The SUC2 fusion vector pSEYC308 was described previously (26). The EcoRI-SalI amplified DNA fragments were cloned into the unique EcoRI and SalI sites of pSEYC308 to generate the hybrid proteins GPI-39 and GPI-354. The construction of the PHO8-SUC2 gene fusion plasmid containing the amino-terminal 191 amino acids of alkaline phosphatase fused to invertase, API-191, was described previously (27). The PEP4-SUC2 gene fusions, P4I-23 and P4I-137, containing portions of proteinase A fused to invertase were described previously (26).

Assays. Invertase and glucose detection assays were done as described previously (17). At each time point to be assayed, approximately 2 units of cells at an optical density at 600 nm of 1.0 were centrifuged and the supernatant fraction removed for determination of the remaining glucose concentration. The cells were washed in 10 mM sodium azide, centrifuged and resuspended in 0.5 ml of 0.1 M sodium acetate, pH 5.0. An aliquot of the resuspended cells was removed to determine the optical density of the resuspended culture and the remaining cells were lysed by the addition of Triton X-100 (0.5% final concentration) followed by freezing in dry ice. Invertase assays were performed using 0.0025–0.2 optical density units of cells. One optical density unit of cells corresponds to approximately $1 \times 10^7$ yeast cells or 200 μg of protein.

To quantitate secretion of hybrid proteins, intact and detergent-permeabilized cells synthesizing the GPI-39, GPI-354, P4I-23 or P4I-137 hybrid proteins were assayed for invertase activity (26). Yeast cells were harvested in respiro-fermentative (mid-logarithmic) or respiratory phase and collected by centrifugation. The cells were washed in 10 mM sodium azide, resuspended in 0.1 M sodium acetate, pH 5.1 and divided into two aliquots. A sample was measured to determine the optical density. One aliquot was held on ice (intact cells). Triton X-100 (0.5% final concentration) was added to the remaining aliquot followed by freeze/thaw in dry ice (lysed cells). Invertase activities were carried out and the percent secreted invertase was determined by dividing the activity detected in intact cells by the total activity detected in lysed cells.

The percentage of ethanol in the growth media was determined by chromatography on a Hewlett Packard 5710A gas chromatograph using a Supelco TightSpec glass column with 80/120 Carbopack B AW packing and 5% Carbowax 20M coating.

Nucleotide sequence accession number. The sequence of the YGP1 gene iss been assigned EMBL number X73030 *S. cerevisiae* YGP1 gene.

RESULTS

Cloning and sequencing of YGP1

Previous studies of the vacuolar enzyme acid trehalase led to the purification and initial characterization of a highly glycosylated protein that was shown to transit through the secretory pathway (36, 37). To further characterize this enzyme we initiated experiments designed to clone the gene, designated ATH1, encoding this vacuolar hydrolase. As a first step, a protein preparation having high acid trehalase activity was purified from the yeast *Saccharomyces cerevisiae*, as described previously (36). Highly glycosylated proteins such as acid trehalase and invertase are difficult to separate under the conditions used in the purification, necessitating the use of a suc2 mutant strain. The protein purification procedure resulted in a 7,174-fold increase in the specific activity of acid trehalase (36).

Four peptide fragments derived from an endoproteinase Lys-C digestion of the purified protein preparation were sequenced by Edman degradation. Based on the sequence information, degenerate oligonucleotides were prepared corresponding to the amino terminus and an internal peptide fragment. Amplification of yeast genomic DNA with PCR produced a 500 bp fragment that contained a single open reading frame. The open reading frame encoded both of the peptide sequences upon which the degenerate oligonucleotides were based. To recover the full-length gene, the 500 bp fragment was used to probe a genomic DNA library as described in Materials and Methods. Four plasmids were obtained by colony hybridization that had an overlapping 1.9 kbp HindIII restriction enzyme fragment. The sequence of the 1.9 kbp fragment is shown in FIG. 1 (SEQ ID NO:1) along with additional sequence information from the 5' non-coding region.

The entire 1.9 kbp fragment has a single open reading frame of 1,062 bp. The 5' non-coding region contains two possible TATA boxes and there is a putative polyadenylation signal 340 bp downstream of the stop codon in the 3' untranslated region. The open reading frame encodes a 354 amino acid protein (SEQ ID NO:2) with a predicted molecular weight based on the deduced amino acid sequence of approximately 37,381 Da. The first twenty amino terminal residues have a sequence which fits with the normal hydrophobic consensus for signal peptides. In addition, there are two sequences in this region that contain possible signal sequence cleavage sites based on the rules of von Heijne (52). The site with the highest probability of cleavage is between amino acid residues 19 and 20 (S value of 8.66). The coding region contains fourteen potential N-glycosylation sites. Eleven of these are the more commonly used Asn-X-Thr sequence (38) suggesting that the protein might undergo extensive carbohydrate modification. The gene was named YGP1, for yeast glycoprotein. Based on the deduced molecular weight and glycosylation (see below), the gene product was named gp37 for 37 kDa glycoprotein.

The YGP1 gene does not encode acid trehalase

The peptides that were the basis for the degenerate oligonucleotides used in the cloning of YGP1 were derived from a protein preparation having high acid trehalase activity (36). We will refer to this protein preparation as acid trehalase/gp37. Our results indicate that YGP1 is not the structural gene for acid trehalase. Acid trehalase is a vacuolar protein (25, 33, 36). None of the well characterized vacuolar proteins show the extensive glycosyl modifications that are typical of proteins such as invertase and acid phosphatase (1, 28, 29). The protein characterized by Mittenbühler and Holzer (36, 37) is highly glycosylated and migrates with an apparent molecular weight of 220 kDa. This type of extensive glycosylation would be unexpected for vacuolar acid trehalase. Similarly, native gp37 migrated as a high molecular-weight smear on SDS-polyacrylamide gels. This mobility is characteristic of highly glycosylated proteins and likely reflects a heterogeneous mixture of gp37 molecules with variable length outer mannose carbohydrate chains. Deglycosylation of gp37 produced a discrete species which migrated at approximately 41 kDa. This apparent molecular weight is in close agreement with the predicted size of the YGP1 gene product based on the deduced amino acid sequence.

To further test the identity of gp37 with acid trehalase, we constructed a yeast strain that was disrupted for the chromosomal YGP1 gene. A strain disrupted at the YGP1 locus, MDY1 (Δygp1::URA3), was constructed by insertion of the URA3 gene at the HpaI site of YGP1 as described in Materials and Methods above. The correct integration was confirmed by Southern blot. The disrupted mutant was fully active for acid trehalase. Further, gp37 was not detected in protein extracts from this strain, and antibodies prepared against gp37 do not precipitate acid trehalase activity from yeast cytosol. Finally, we show that gp37 is a secreted protein which is not consistent with it being localized to the vacuole. Perhaps as the result of similar physical properties such as a high degree of glycosylation or the nature of acid trehalase as a sugar binding protein, acid trehalase and gp37 copurified in the preparation described by Mittenbühler and Holzer (36). In any event, our data indicate that YGP1 is not the structural gene for acid trehalase and gp37 is not the vacuolar acid trehalase.

YGP1 is homologous to a sporulation-specific protein

The deduced amino acid sequence from the YGP1 gene was compared to proteins in the SWISS-PROT and PIR protein data bases using the FASTA algorithm and Wordsearch program of the Wisconsin Genetics Computer Group Package (10). This analysis revealed significant homology between gp37 and a sporulation-specific protein that is the product of the SPS100 gene (30). These two proteins show 50% identity and 67% overall similarity over their entire lengths. The similarity is greatest over the C-terminal half of the two proteins. The SPS100 gene was identified by screening with sporulation-specific RNA probes to identify genes that are expressed near the completion of sporulation. SPS100 RNA appears 35 hours after transfer of diploid cells to sporulation medium. A mutation in SPS100 resulted in one detectable phenotype; spores from the mutant strain were less resistant to diethyl ether suggesting a role for the gene product in spore wall formation.

Expression of YGP1 is subject to glucose repression

Due to the homology of YGP1 with SPS100, we decided to examine expression of the YGP1 gene during different phases of growth. We examined expression of the YGP1 gene during respiro-fermentative (logarithmic) and respiratory phase by determining the levels of YGP1-specific mRNA present at various time points of growth. Strain SEY6210 cells were grown in YPD medium containing 2% glucose. At various times, aliquots of the culture were removed and the presence of YGP1-specific mRNA was analyzed by Northern blot as described in Materials and Methods, above. The YGP1 gene is expressed at low levels during respiro-fermentative (logarithmic) growth. Exit from this phase of growth and entry into the respiratory phase (marked by depletion of glucose and growth on ethanol) in a haploid strain is accompanied) by an increased level of expression of YGP1-specific RNA as revealed by Northern blot. The bulk 18S and 25S rRNA species served as controls and showed that essentially equivalent amounts of RNA were analyzed at each time point.

Since YGP1-specific RNA is not expressed at high levels in cells during respiro-fermentative (logarithmic) growth, we decided to examine synthesis of the gp37 protein during different growth phases. To examine synthesis of gp37, protein extracts were prepared from yeast cells at different stages of growth and analyzed by Western blot. We found that the protein is present at a low level in extracts prepared from logarithmically growing cells. In contrast, when respiratory phase cells were examined there was a substantial increase in the level of gp37. This result correlated with the Northern blot analysis of YGP1-specific RNA demonstrating that regulation of expression occurred primarily at the transcriptional rather than the translational level.

The Western blot analysis indicated that synthesis of gp37 is subject to repression by high glucose concentrations. To carefully quantify the reduction in glucose concentration that is necessary to allow expression of YGP1, we examined the regulation of expression through the use of hybrid proteins. Portions of YGP1 encoding either the first 39 amino acids (GPI-39) or the full length protein (GPI-354) or alkaline phosphatase (API-191) were fused to a fragment of the yeast SUC2 gene encoding invertase as described in Materials and Methods. The truncated SUC2 gene that is present in these constructs lacks the promoter region and amino terminal signal sequence. In the gene fusions, expression of invertase activity is therefore controlled by the YGP1 regulatory elements. Plasmids encoding the hybrid proteins were transformed into a strain bearing a deletion of the chromosomal SUC2 locus. Yeast cells were grown in YNB medium containing either 2% or 3% glucose as indicated. The optical density of the culture was determined and samples were removed at various time points. The invertase activity corresponding to the hybrid proteins and the glucose concentration remaining in the medium were determined for each sample as described in Materials and Methods. Units of invertase activity are defined as nanomoles of glucose released per minute per one optical density unit of cells.

Figure 2B:
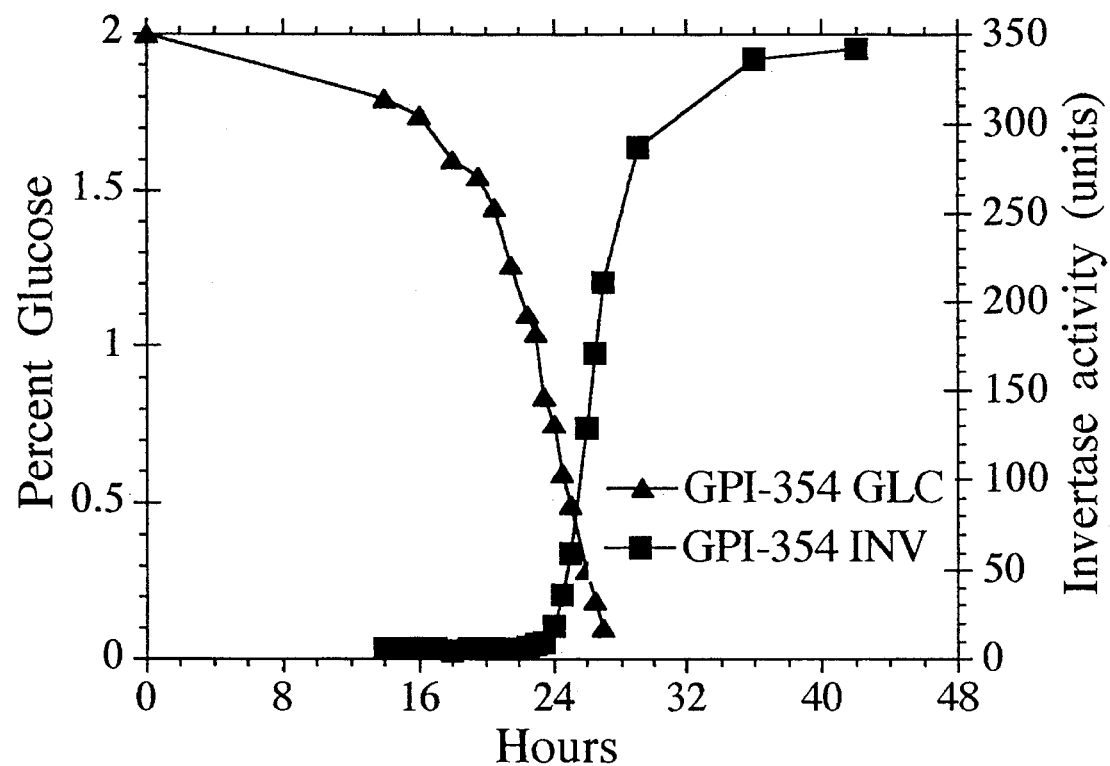
Figure 2C:
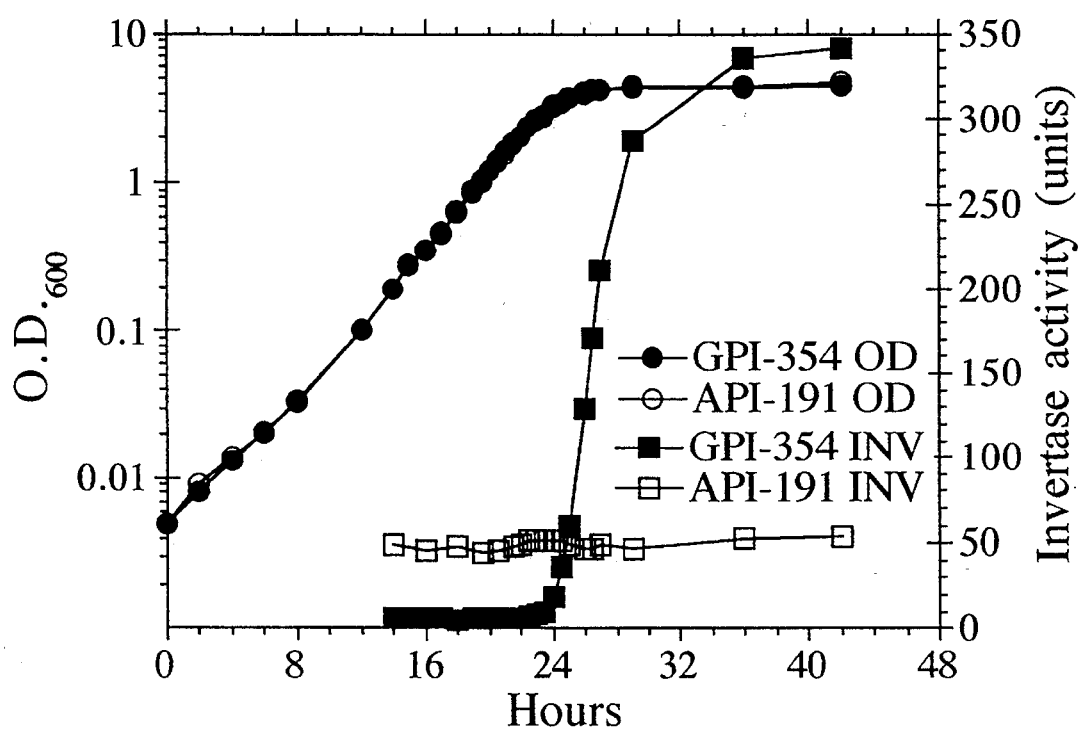
Figure 2D:
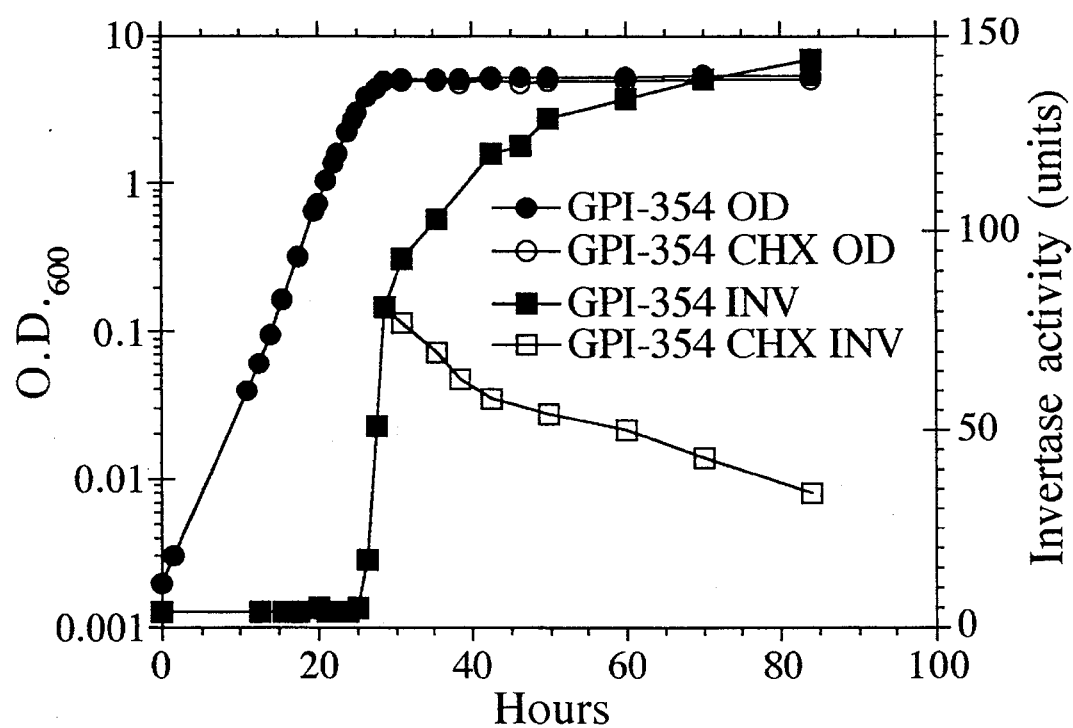

The results with the hybrid proteins were in agreement with the Northern blot analysis of YGP1-specific mRNA and our observations of the authentic gp37 protein. During logarithmic growth, a basal level of invertase activity was seen corresponding to either the GPI-39 or GPI-354 hybrid proteins (FIG. 2A). When the level of glucose in the medium dropped to 1%, increased invertase activity was detected (FIG. 2B). This corresponded with the results from the Northern analysis which indicated that YGP1-specific mRNA was detectable only when the glucose dropped from 1.6% to 0.96%. The invertase activity from the gp37-invertase hybrid proteins continued to increase during the diauxic lag phase and remained steady during part of the respiratory phase. The invertase activity peaked approximately 60–80 hours after growth had reached a plateau (FIG. 2D). The maximal activity seen was approximately 50 fold above the basal level.

We decided to determine whether the increased activity was the result of de novo protein synthesis. Cultures of yeast harboring the plasmid encoding the GPI-354 hybrid protein were grown in synthetic medium with 2% glucose. When the glucose level dropped below 1%, cycloheximide was added to one of the cultures. Invertase activity did not increase after addition of cycloheximide (FIG. 2D). Instead, there was a slow decrease in activity that may reflect the normal turnover of gp37.

When cells exhaust a limiting nutrient they may enter into stationary phase. Entry into stationary phase results in changes that provide increased resistance to stress. These physiological adaptations, however, do not necessarily depend on the growth phase of the cells but rather on the growth rate (13). To determine if expression of YGP1 was triggered by some aspect of growth rate or by glucose depletion, we grew yeast under conditions where glucose was in excess and growth was limited by the availability of an auxotrophic amino acid.

Figure 2E:
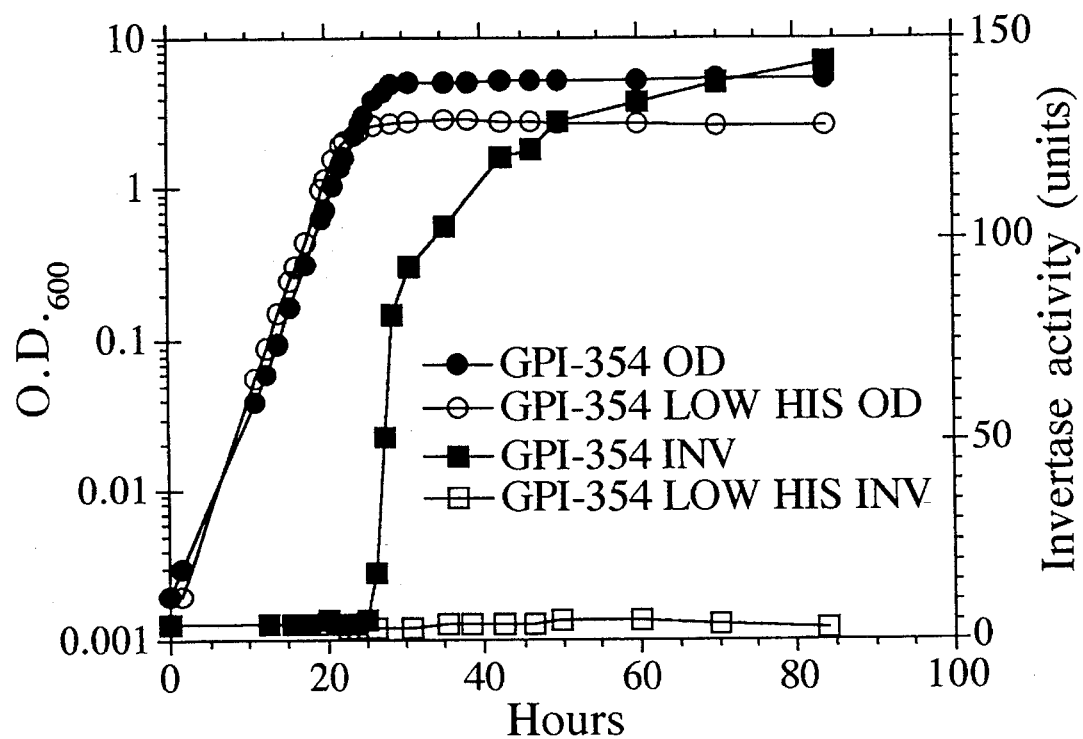
Figure 2F:
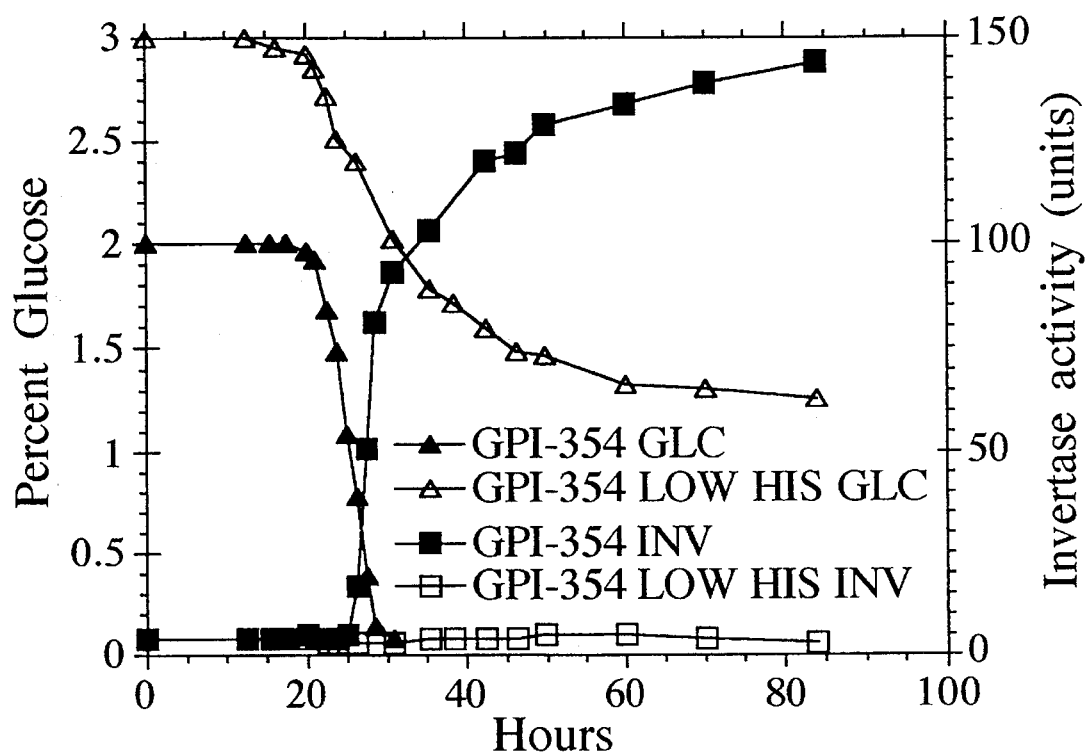

A yeast strain auxotrophic for histidine was grown in synthetic medium containing either limiting glucose and the necessary amino acids or a non-limiting concentration of glucose and a limiting concentration of histidine. When the auxotrophic amino acid became limiting the cells ceased growing (FIG. 2E,F). The glucose in this culture did not drop below 1%. Under these conditions, YGP1-dependent expression of invertase did not increase. This suggests that the increase in invertase activity regulated by the YGP1 promoter does not correspond to slow growth or a cessation of growth per se but rather to glucose depletion. In addition, the increase in activity is not due to non-specific starvation effects. Alkaline phosphatase, the product of the PHO8 gene (24, 51), is regulated by phosphate through the interaction of several PHO genes (reviewed in 39). An alkaline phosphatase-invertase hybrid protein does not show elevated expression upon glucose depletion (FIG. 2C).

Expression of YGP1 is not regulated by the general glucose control of the SNF1 pathway Many genes that are subject to catabolite repression can be derepressed upon shifting the growing culture to medium containing non-repressing levels of glucose. We tested the effect of this type of acute change in glucose levels on the expression of YGP1. Yeast cells harboring a plasmid encoding GPI-354 were grown in YNB medium with 2% glucose. During respiro-fermentative (logarithmic) phase growth portions of the culture were removed, the cells collected by centrifugation and resuspended in fresh YNB medium with 0.05% or 0.1% glucose. The cultures were incubated an additional 136 hrs and samples were removed at 12 hour intervals to assay for invertase activity. We found that expression of YGP1 was not increased when cells were shifted directly to low glucose media.

The absence of elevated expression of YGP1 when cells are shifted to low glucose suggests that the gene may be regulated by a unique type of glucose repression. We tested whether YGP1 was regulated by the general glucose control pathway which utilizes SNF1 (23). A yeast strain disrupted at the chromosomal SNF1 locus was transformed with a plasmid encoding the GPI-354 hybrid protein. Cells were grown beyond the point of glucose depletion and assayed for invertase activity. In both wild type and snf1 mutant cells, the invertase activity from the GPI-354 hybrid protein increased when glucose was depleted from the medium. In the snf1 strain, the activity reached a level 50–60% of that seen in the SNF1 wild type strain. This level of invertase activity corresponds to an approximately 17 fold increase above the basal invertase activity seen during respiro-fermentative (logarithmic) phase growth. In a control experiment, the snf1 mutant cells were unable to derepress synthesis of invertase from a plasmid encoding the wild type SUC2 gene under the control of its endogenous promoter. Derepression of YGP1 is apparently not dependent on a functional SNF1 gene product.

Expression of YGP1 is elevated in response to multiple signals

To determine if expression of YGP1 is regulated only by the glucose concentration or by more general nutrient limitation, we examined expression of the gp37-invertase hybrid proteins under conditions of limiting phosphate, sulfate and nitrogen. Yeast cells harboring the plasmid encoding GPI-354 were grown in modified Wickerham's minimal medium having 4–5% glucose and varying phosphate, sulfate or nitrogen concentrations as described in Materials and Methods. Samples were removed at various times during growth corresponding to respiro-fermentative (logarithmic), diauxic lag and respiratory phases of growth. The cells at each time point were assayed for invertase activity to assess expression of YGP1, and the medium was assayed to determine the glucose concentration.

Figure 3A:
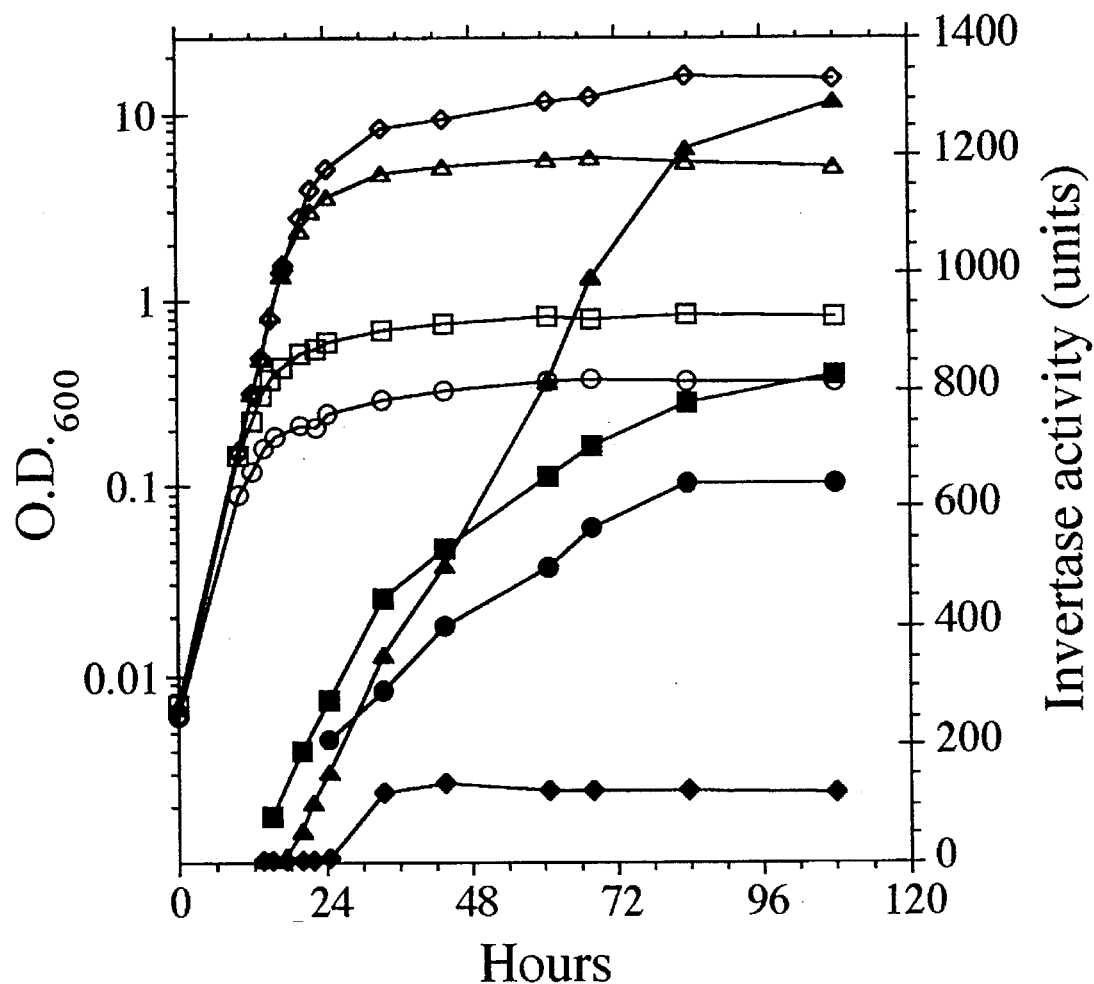
FIGS. 3(A)–3(B). The YGP1 gene is regulated by the phosphate concentration. Yeast strain SEY2108 transformed with a plasmid encoding the GPI-354 hybrid protein was grown in minimal medium as described in Materials and Methods (medium E) with initial potassium phosphate concentrations ([PO$_4$]$_i$) of 0.002–2 mM. Cultures were inoculated to an initial density of approximately 0.01 and samples were removed at the indicated times. At each time point an aliquot of the culture was removed, the invertase activity corresponding to the GPI-354 hybrid protein and the glucose concentration in the medium were determined as described in Materials and Methods. Invertase activity is expressed as nanomoles of glucose released per minute per one optical density unit of cells. (A) O.D.$_{600}$ and (B) percent glucose versus invertase activity at varying initial phosphate concentrations.
Figure 3B:
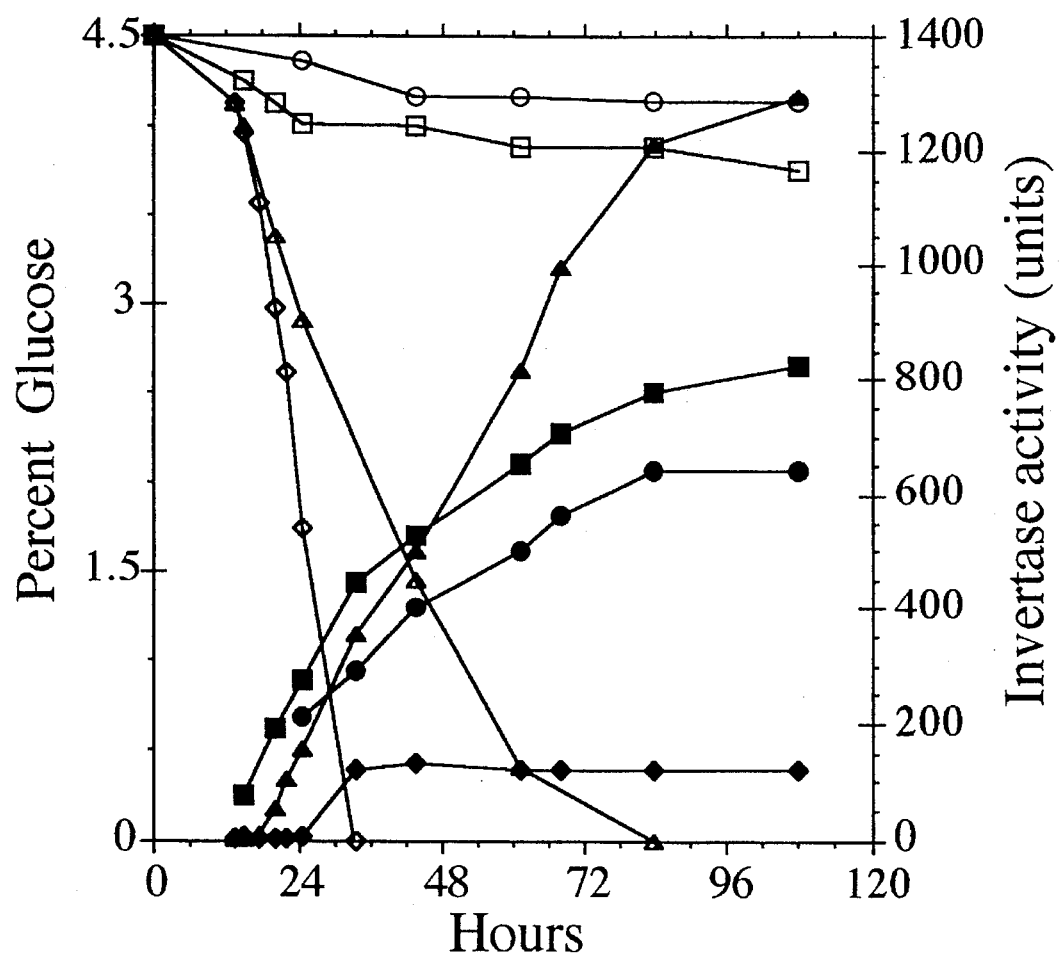

Expression of YGP1 is not dependent solely on the level of glucose. Expression increased in a time-dependent manner at initial phosphate concentrations of 2–20 μM even though the glucose concentration did not drop below approximately 4% (FIG. 3). The maximal level of invertase activity was higher than that seen when cell growth was limited only by glucose. The highest level of YGP1 expression was seen at 0.2 mM initial phosphate. In this case, the invertase activity began to increase before glucose fell below 1%. In contrast to the lower phosphate cultures, however, there was sufficient phosphate to allow growth to eventually deplete the glucose below the 1% level (FIG. 3B). This may have caused a synergistic effect resulting in maximal expression of YGP1 to a level approximately 200 fold above the basal level. At an initial phosphate concentration of 2 mM, expression of YGP1 increased only after the glucose level dropped below 1%.

Figure 4:
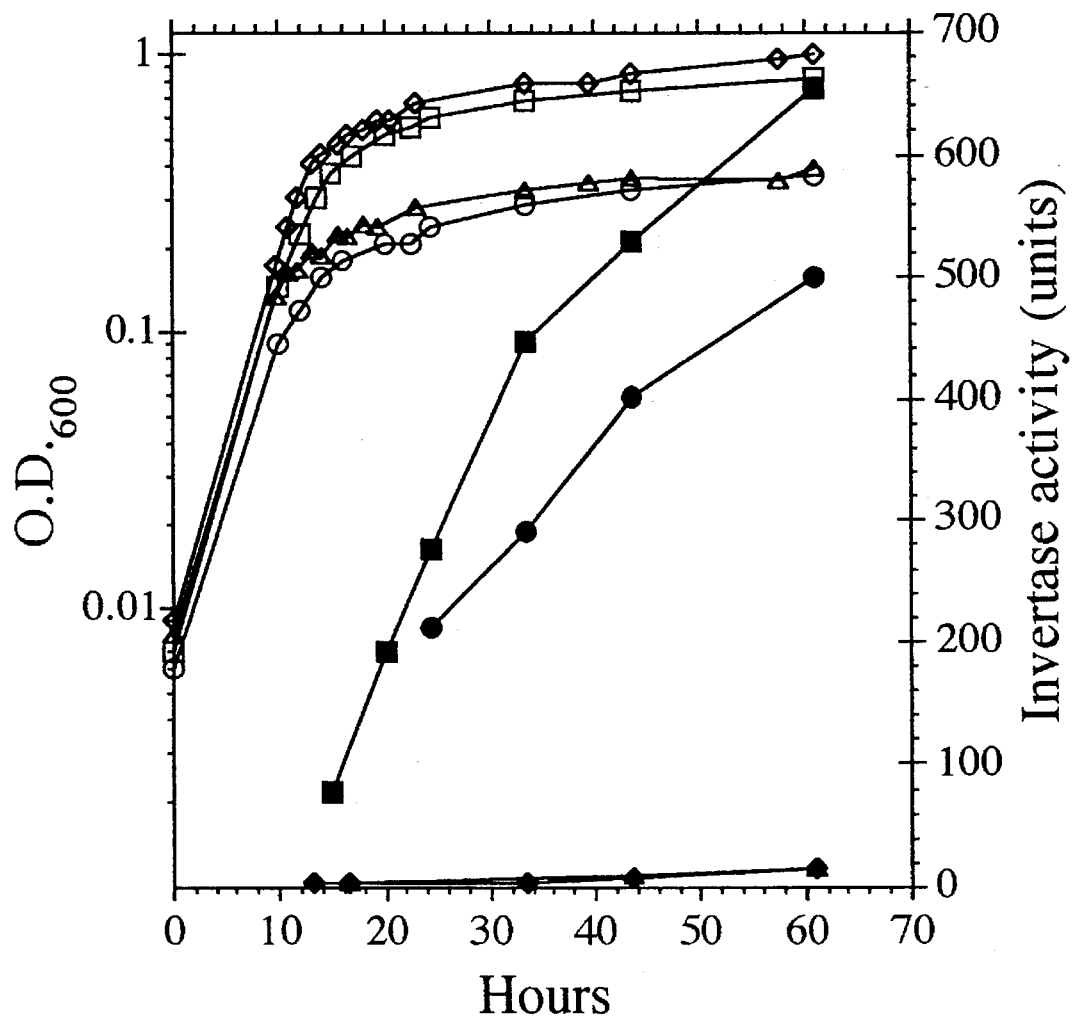
FIG. 4. Limiting sulfate or slow growth do not allow expression of YGP1. Yeast strain SEY2108 transformed with a plasmid encoding the GPI-354 hybrid protein was grown in minimal medium as described in Materials and Methods (medium F) with the initial potassium phosphate ([PO$_4$]$_i$) or magnesium sulfate ([SO$_4$]$_i$) concentrations indicated. Cultures were inoculated to an initial density of approximately 0.005–0.01 and samples were removed at the indicated times. Aliquots of the culture were assayed for invertase and glucose. The glucose level in the medium varied from 3.8–4.5% over the indicated time course for all of the cultures shown. Invertase activity is expressed as nanomoles of glucose released per minute per one optical density unit of cells.

In contrast to the result with limiting phosphate, starvation for sulfate did not cause an increase in YGP1 expression over the time course examined (FIG. 4). Even though the sulfate and phosphate starved cultures showed similar doubling times and growth yields there was a significant difference in the level of invertase activity from the GPI-354 hybrid protein in cells grown under the two conditions. This suggests that growth phase is not the determinant of YGP1 expression in agreement with the results for limiting histidine (FIG. 2E).

Figure 5A:
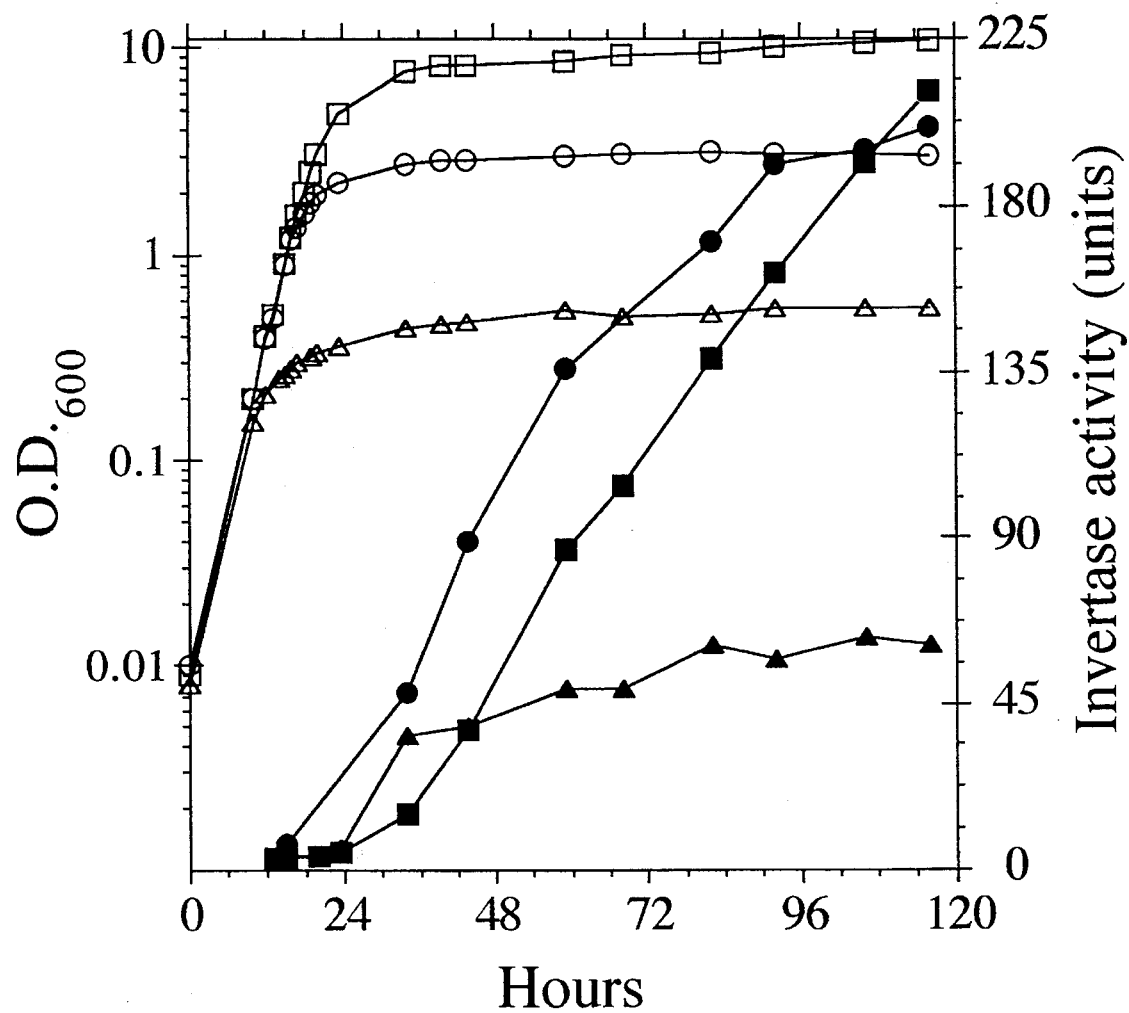
FIGS. 5(A)–5(B). The YGP1 gene is regulated by the nitrogen concentration. Yeast strain SEY2108 transformed with a plasmid encoding the GPI-354 hybrid protein was grown in minimal medium as described in Materials and Methods (medium G) with initial asparagine concentrations ([Asn]$_i$) of 0.002–0.2%. Aliquots of the culture were assayed for invertase and glucose. (A) O.D.$_{600}$ and (B) percent glucose versus invertase activity at varying initial asparagine concentrations.
Figure 5B:
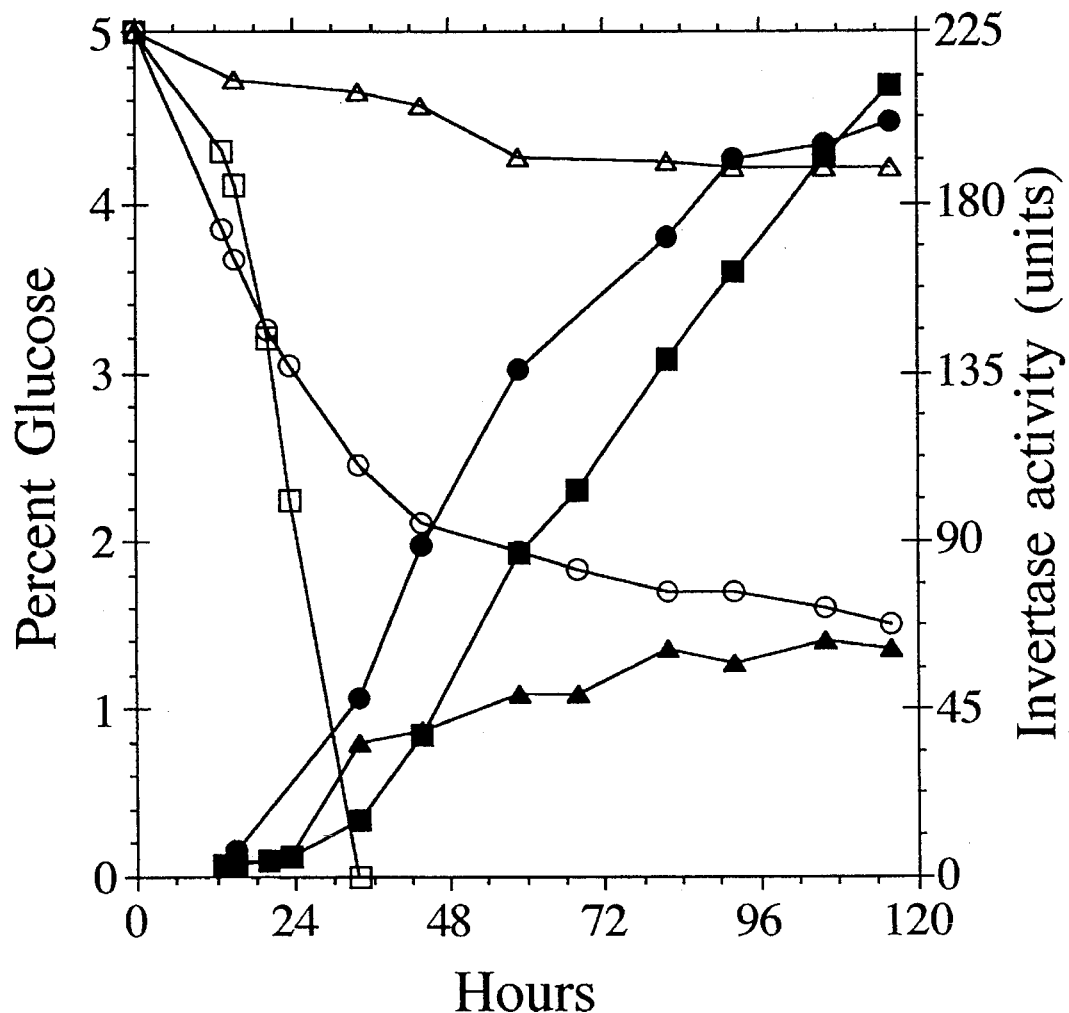

Similar to the results for limiting phosphate, nitrogen depletion allowed expression of YGP1 (FIG. 5). When asparagine was present as the sole nitrogen source at an initial level of 0.002% there was an approximately ten-fold increase in invertase activity above the basal level. This relatively low level of expression is probably due to the overall poor growth of this culture. At 0.02% initial asparagine the expression of YGP1 increased approximately 35 fold even though the glucose remained above 1%. These results suggest that YGP1 is responsive to the limitations of multiple nutrients including phosphate and nitrogen in addition to the carbon/energy source.

The gp37 protein is degraded in the presence of glucose

The synthesis of certain enzymes is repressed by glucose in a process termed catabolite or glucose repression. Many enzymes which are regulated by glucose are also subject to glucose-induced inactivation, sometimes referred to as "catabolite inactivation" (19). This refers to the inactivation of pre-existing enzymes as opposed to the inhibition of new synthesis. This type of nutrient regulation is often the result of proteolysis (20). To examine the possibility of proteolytic inactivation of gp37, cells were grown for 48 hours to deplete the glucose and allow expression of the protein. Glucose was added back to the culture to a final concentration of 3% and the cells were allowed to continue growing. Samples were taken at different time points and used to prepare protein extracts. The extracts were deglycosylated with endoglycosidase H as described in Materials and Methods and analyzed by Western blot.

The gp37 protein was degraded in the presence of glucose. Within eight hours after the addition of fresh glucose to the glucose-depleted cultures there was no detectable gp37. When the glucose had again been depleted from the medium following renewed growth, gp37 was resynthesized. In control cells that did not receive additional glucose, the level of gp37 remained relatively unaffected. The degradation of gp37 seen in the presence of glucose was probably due to a specific process of "nutrient regulation" involving proteolysis and was not likely to reflect the normal turnover rate of the protein in the absence of new synthesis. When synthesis of gp37 was inhibited by cycloheximide the protein was degraded at a greatly reduced rate (FIG. 2D); following the addition of cycloheximide, there was a 50% reduction in invertase activity in approximately 48 hrs. Since certain types of proteolytic inactivation may be blocked in the presence of cycloheximide (15) the decrease in invertase activity seen in the presence of this antibiotic may be an indication of the normal turnover rate of gp37.

The mechanism by which glucose regulates expression of YGP1 appears to be complex since derepression did not occur upon shifting cells to low glucose. To better understand the phenomenon of glucose repression, we examined expression of YGP1 during growth in various non-fermentable carbon/energy sources. Yeast cells harboring the GPI-354 hybrid protein were grown in YNB medium containing either glucose, glycerol/lactate, pyruvate or ethanol as described in Materials and Methods. At various time points aliquots were removed and assayed for invertase activity. In addition, the media were assayed to determine the glucose and/or ethanol levels. Growth in glycerol/lactate or pyruvate did not allow expression of YGP1 (FIG. 6A).

Figure 6A:
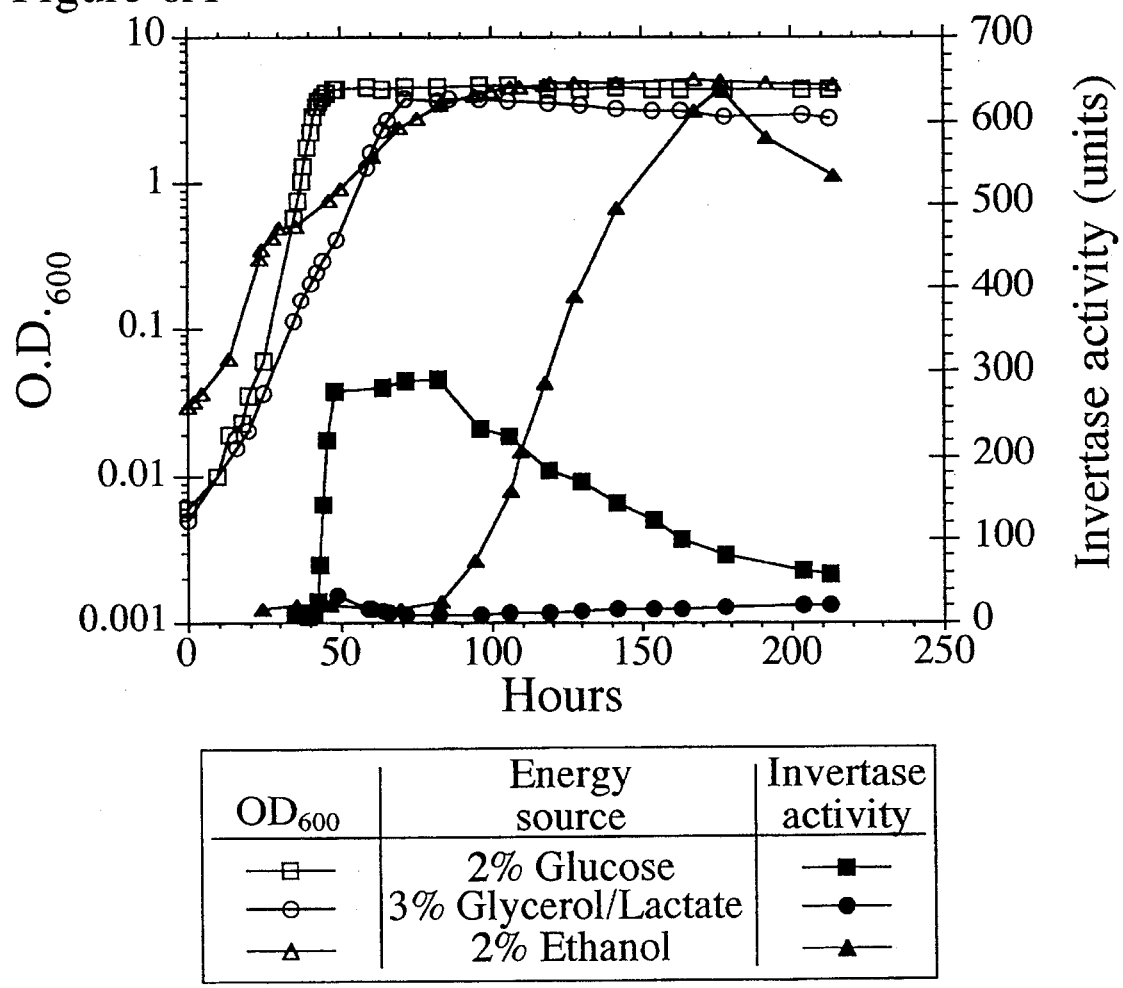
FIGS. 6(A)–6(C). Expression of YGP1 in non-fermentable carbon/energy sources. Yeast strain SEY2108 transformed with a plasmid encoding the GPI-354 hybrid protein was grown in YNB medium containing either 2% glucose, 3% glycerol/lactate or 2% ethanol as indicated. Cells grown in YNB 2% pyruvate showed essentially similar results as those grown in glycerol/lactate. Cultures were inoculated to an initial density of approximately 0.01 and samples were removed at the indicated times. Aliquots of the culture were assayed for invertase, glucose and/or ethanol as described in Materials and Methods. (A) O.D.$_{600}$ and invertase activities for cultures grown in various carbon/energy sources. (B) Glucose and ethanol concentrations versus invertase activity for culture grown in YNB 2% glucose. (C) Ethanol concentration versus invertase activity for culture grown in YNB 2% ethanol.
Figure 6B:
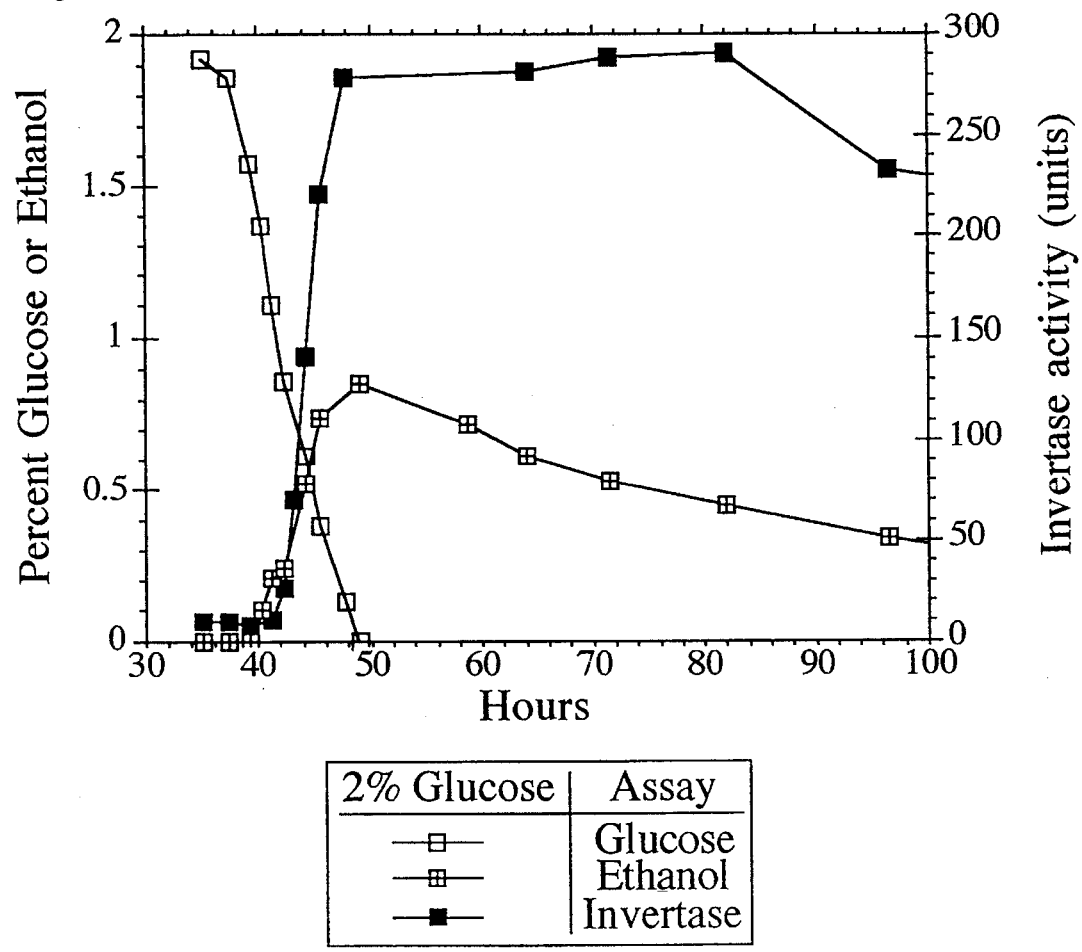
Figure 6C:
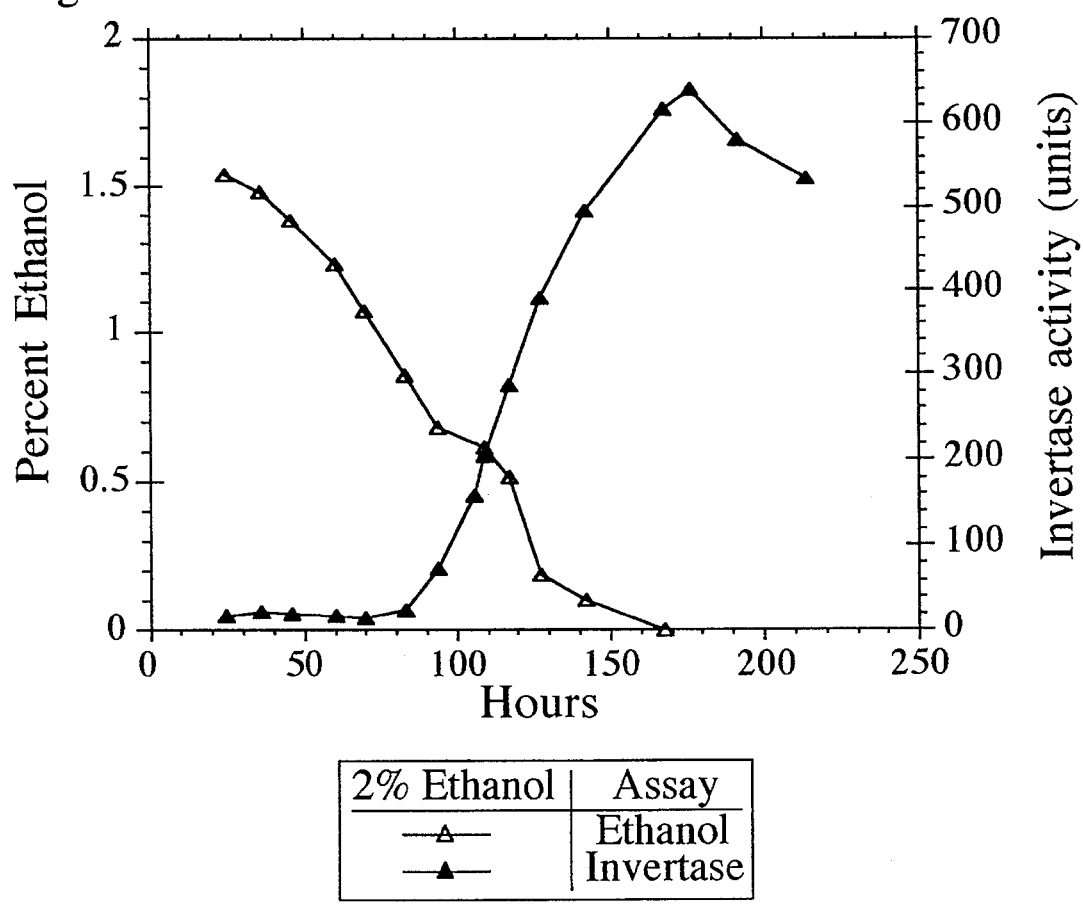

In contrast to glycerol/lactate and pyruvate, cells grown in ethanol showed an approximately 100 fold increase in invertase activity above the basal level (FIG. 6A). The observed increase did not reflect derepression in the usual sense in that the increase in activity did not occur for approximately 3 days following growth in ethanol. The increase in expression occurred when the ethanol level dropped to 0.8–1% (FIG. 6C). It should be noted that when cells were grown in 2% glucose, the ethanol level remained below the 0.8–1% range (FIG. 6B).

Localization of gp37

The number of potential glycosylation sites indicate that gp37 is highly glycosylated. This was confirmed by gp37 migrating as a heterogeneously highly glycosylated protein. In fact, gp37 is one of the most highly glycosylated yeast proteins on a weight to weight basis. The apparent molecular weight of gp37 (36, 37) and the number of potential glycosylation sites suggested that there may be an average of approximately 90 mannose residues per carbohydrate side chain.

As discussed earlier, gp37 is predicted to have a signal sequence cleavage site between amino acid residues 19 and 20. The mature protein apparently begins at residue 38 based on amino acid sequencing of the purified protein. This may indicate additional processing subsequent to removal of the signal sequence or degradation during the purification procedure.

We examined the location of the gp37-invertase hybrid proteins in yeast cells that were repressed or derepressed for the expression of YGP1. Cells harboring plasmids encoding either the GPI-39 or GPI-354 hybrid proteins were grown in synthetic medium containing 2% glucose. In addition, we analyzed two control proteins, P4I-23 and P4I-137, which contain portions of proteinase A fused to invertase (26). P4I-23 has only the signal sequence portion of proteinase A and serves as a control for a secreted protein. P4I-137 includes a segment of proteinase A that contains the vacuolar sorting information. This hybrid protein is eficiently targeted to the vacuole and provides a control for a non-secreted protein.

Samples of cells were removed during respiro-fermentative (logarithmic) phase or respiratory phase growth and assayed for secreted versus total invertase activity as described in Materials and Methods. In either case, approximately 80–100% of the invertase activity corresponding to the gp37-invertase hybrid proteins were secreted into the periplasm (Table 1).

TABLE 1

| Hybrid protein | Secretion of hybrid proteins | | |
|---|---|---|---|
| | Invertase activity (units) | | Percent |
| | Intact cells | Lysed cells | secreted |
| GPI-354[a] | 12 | 14 | 86% |
| GPI-354 | 172 | 209 | 82% |
| GPI-39 | 217 | 221 | 98% |
| P4I-23 | 534 | 515 | 104% |
| P4I-137 | 21 | 319 | 7% |

*The invertase assay was performed on cells in respiro-fermentative (logarithmic) phase growth. All other assays were carried out on respiratory (post-glucose exhaustion) phase cells.

Immunoprecipitation of radiolabeled cells indicated that the hybrid proteins were stable for at least one hour. Since secretion in yeast is rapid, the above results with GPI-39 and GPI-354 reflected gp37 localization and not that of a degraded hybrid protein. This extracellular localization further suggested that YGP1 does not encode the vacuolar enzyme acid trehalase. The extracellular location also fits with the extensive glycosylation seen on gp37, which is similar to certain other secreted proteins (1, 29).

Regulation of YGP1 is unique from that of other genes which are subject to glucose repression. For example, the gp37 protein is not synthesized when logarithmically growing cells are shifted to 0.05–0.1% glucose or when cells are grown in non-fermentable carbon/energy sources. In addition, YGP1 is regulated by a more general nutrient sensing process. Increased expression of YGP1 in response to the limitation of various nutrients fits with the observation that entry into stationary phase and the accompanying physiological changes occur in response to limiting nitrogen, phosphorus or glucose (12, 32, 41). The expression of YGP1 is regulated in response to specific nutrient levels and not by growth rate. The latter was demonstrated by the lack of elevated expression when cells exit the respiro-fermentative (logarithmic) growth phase as a result of limiting histidine or limiting sulfate. This fits with the observation that stress resistance is independent of the cell cycle (13).

LITERATURE CITED

1. Ballou, C. E. 1982. Yeast cell wall and cell surface. In Strathern, J. N., Jones, E. W. and Broach, J. R. (Eds.),The Molecular Biology of the Yeast Saccharomyces: Metabolism and Gene Expression. Cold Spring Harbor Laboratory, Cold Spring Harbor, N.Y. pp 335–360.
2. Bankaitis, V. A., L. M. Johnson, and S. D. Emr. 1986. Isolation of yeast mutants defective in protein targeting to the vacuole. Proc. Natl. Acad. Sci. USA 83:9075–9079.
3. Birnboim, H. C., and J. Doly. 1979. A rapid alkaline extraction procedure for screening recombinant plasmid DNA. Nucl. Acids Res. 7:1513–1523.
4. Boucherie, H. 1985. Protein synthesis during transition and stationary phases under glucose limitation in Saccharomyces cerevisiae. J. Bacteriol. 161:385–392.
5. Casadaban, M. J., and S. N. Cohen. 1980. Analysis of gene control signals by DNA fusion and cloning in Escherichia coli. J. Mol. Biol. 138:179–207.
6. Chirgwin, J. M., A. E. Przybyla, R. J. MacDonald, and W. J. Rutter. 1979. Isolation of biologically active ribonucleic acid from sources enriched in ribonuclease. Biochemistry 18:5294–5299.
7. Compton, T. 1990. Degenerate primers for DNA amplification. In Innis, M. A., Gelfand, D. H., Sninsky, J. J. and White, T. J. (Eds.), PCR Protocols. A Guide to Methods and Applications. Academic Press, Inc., San Diego. pp 39–45.
8. De Nobel, J. G., F. M. Klis, J. Priem, T. Munnik, and H. van den Ende. 1990. The glucanase-soluble mannoproteins limit cell wall porosity in Saccharomyces cerevisiae. Yeast 6:491–499.
9. Deutch, C. E., and J. M. Parry. 1974. Sphaeroplast formation in yeast during the transition from exponential phase to stationary phase. J. Gen. Microbiol. 80:259–268.
10. Devereux, J., P. Haeberli, and O. Smithies. 1984. A comprehensive set of sequence analysis programs for the VAX. Nucl. Acid. Res. 12:387–395.
11. Dodyk, F., and A. Rothstein. 1964. Factors influencing the appearance of invertase in Saccharomyces cerevisiae. Arch. Biochem. Biophys. 104:478–486.
12. Drebot, M. A., C. A. Barnes, R. A. Singer, and G. C. Johnston. 1990. Genetic assessment of stationary phase for cells of the yeast Saccharomyces cerevisiae. J. Bacteriol. 172:3584–3589.
13. Elliott, B., and B. Futcher. 1993. Stress resistance of yeast cells is largely independent of cell cycle phase. Yeast 9:33–42.
14. Feinberg, A. P., and B. Vogelstein. 1983. A technique for radiolabelling DNA restriction endonuclease fragments to high specific activity. Anal. Biochem. 132:6–13.
15. Ferguson Jr., J. J., M. Boll, and H. Holzer. 1967. Yeast malate dehydrogenase: enzyme inactivation in catabolite repression. Eur. J. Biochem. 1:21–25.
16. Finley, D., E. Özkaynak, and A. Varshavsky. 1987. The yeast polyubiquitin gene is essential for resistance to high temperature, starvation, and other stresses. Cell 48:1035–1046.
17. Goldstein, A., and J. O. Lampen. 1975. b-D-Fructofuranosidase fructohydrolase from yeast. Methods Enzymol. 42:504–511.
18. Harris, S. D. and D. A. Cotter. 1988. Transport of yeast vacuolar trehalase to the vacuole. Can. J. Microbiol. 34:835–838.
19. Holzer, H. 1976. Catabolite inactivation in yeast. Trends Biochem. Sci. 1:178–181.
20. Holzer, H. 1989. Proteolytic catabolite inactivation in Saccharomyces cerevisiae. Cell Biol. Rev. 21:305–318.
21. Hubbard, E. J., X. L. Yang, and M. Carlson. 1992. Relationship of the cAMP-dependent protein kinase pathway to the SNF1 protein kinase and invertase expression in Saccharomyces cerevisiae. Genetics 130:71–80.
22. Ito, H., Y. Fukuda, K. Murata, and K. Kimura. 1983. Transformation of intact yeast cells treated with alkali cations. J. Bacteriol. 153:163–168.
23. Johnston, M., and M. Carlson. 1992. Regulation of carbon and phosphate utilization. In Jones, E. W., Pringle, J. R. and Broach, J. R. (Eds.), The Molecular Biology of the Yeast Saccharomyces. Gene Expression. Cold Spring Harbor Laboratory Press, Cold Spring Harbor, N.Y. pp 193–281.
24. Kaneko, Y., A. Toh-e, and Y. Oshima. 1982. Identification of the genetic locus for the structural gene and a new regulatory gene for the synthesis of repressible alkaline phosphatase in Saccharomyces cerevisiae. Mol. Cell. Biol. 2:127–137.
25. Keller, F., M. Schellenberg, and A. Wiemken. 1982. Localization of trehalase in vacuoles and of trehalose in the cytosol of yeast (Saccharomyces cerevisiae). Arch. Microbiol. 131:298–301.
26. Klionsky, D. J., L. M. Banta, and S. D. Emr. 1988. Intracellular sorting and processing of a yeast vacuolar hydrolase: Proteinase A propeptide contains vacuolar targeting information. Mol. Cell. Biol. 8:2105–2116.

27. Klionsky, D. J., and S. D. Emr. 1990. A new class of lysosomal/vacuolar protein sorting signals. J. Biol. Chem. 265:5349–5352.

28. Klionsky, D. J., P. K. Herman, and S. D. Emr. 1990. The fungal vacuole: composition, function and biogenesis. Micro. Rev. 54:266–292.

29. Kozulic, B., S. Barbaric, B. Ries, and P. Mildner. 1984. Study of the carbohydrate part of yeast acid phosphatase. Biochem. Biophys. Res. Comm. 122: 1083–1090.

30. Law, D. T. S., and J. Segall. 1988. The SPS100 gene of *Saccharomyces cerevisiae* is activated late in the sporulation process and contributes to spore wall maturation. Mol. Cell. Biol. 8:912–922.

31. Lewis, J. G., C. J. Northcott, R. P. Learmonth, P. V. Attfield, and K. Watson. 1993. The need for consistent nomenclature and assessment of growth phases in diauxic cultures of *Saccharomyces cerevisiae*. J. Gen. Micro. 139:835–839.

32. Lillie, S. H., and J. R. Pringle. 1980. Reserve carbohydrate metabolism in *Saccharomyces cerevisiae*: responses to nutrient limitation. J. Bacteriol. 143:1384–1394.

33. Londesborough, J., and K. Varimo. 1984. Characterization of two trehalases in baker's yeast. Biochem. J. 219:511–518.

34. Lowry, O. H., N. J. Rosebrough, A. L. Farr, and R. J. Randall. 1951. Protein measurements with the Folin phenol reagent. J. Biol. Chem. 193:265–275.

35. Miller, J. 1972. Experiments in molecular genetics. Cold Spring Harbor Laboratory, Cold Spring Harbor, N.Y.

36. Mittenbühler, K., and H. Holzer. 1988. Purification and characterization of acid trehalase from the yeast suc2 mutant. J. Biol. Chem. 263:8537–8543.

37. Mittenbühler, K., and H. Holzer. 1991. Characterization of different forms of yeast acid trehalase in the secretory pathway. Arch. Microbiol. 155:217–220.

38. Moehle, C. M., R. Tizard, S. K. Lemmon, J. Smart, and E. W. Jones. 1987. Protease B of the lysosomelike vacuole of the yeast *Saccharomyces cerevisiae* is homologous to the subtilisin family of serine proteases. Mol. Cell. Biol. 7:4390–4399.

39. Oshima, Y. 1982. Regulatory circuits for gene expression: the metabolism of galactose and phosphate. In Strathern, J. N., Jones, E. W. and Broach, J. R. (Eds.), The Molecular Biology of the Yeast Saccharomyces: Metabolism and Gene Expression. Cold Spring Harbor Laboratory, Cold Spring Harbor, N.Y. pp 159–180.

40. Plesset, J., J. R. Ludwig, B. S. Cox, and C. S. McLaughlin. 1987. Effect of cell cycle position on thermotolerance in *Saccharomyces cerevisiae*. J. Bacteriol. 169: 779–784.

41. Pringle, J. R., and L. H. Hartwell. 1981. The *Saccharomyces cerevisiae* cell cycle. In Strathern, J. N., Jones, E. W., and Broach, J. R. (Eds), The Molecular Biology of the Yeast Saccharomyces: Life Cycle and Inheritance. Cold Spring Harbor Laboratory, New York, pp. 97–142.

42. Robinson, J. S., D. J. Klionsky, L. M. Banta, and S. D. Emr. 1988. Protein sorting in *Saccharomyces cerevisiae*: isolation of mutants defective in the delivery and processing of multiple vacuolar hydrolases. Mol. Cell. Biol. 8:4936–4948.

43. Rose, M. D., P. Novick, J. H. Thomas, D. Botstein, and G. R. Fink. 1987. A *Saccharomyces cerevisiae* genomic plasmid bank based on a centromere-containing shuttle vector. Gene 60:237–243.

44. Sambrook, J., T. Maniatis, and E. F. Fritsch. 1989. Molecular cloning: a laboratory manual, 2nd ed. Cold Spring Harbor Laboratory, Cold Spring Harbor, N.Y.

45. Sanchez, Y., J. Taulien, K. A. Borkovich, and S. Lindquist. 1992. Hsp104 is required for tolerance to many forms of stress. EMBO J. 11:2357–2364.

46. Sanger, F., S. Niclen, and A. R. Coulson. 1977. DNA sequencing with chain-terminating inhibitors. Proc. Natl. Acad. Sci. USA 76:5463–5467.

47. Shahin, M. M. 1972. Relationship between yield of protoplasts and growth phase in Saccharomyces. J. Bacteriol. 110:769–771.

48. Sherman, F., G. R. Fink, and C. W. Lawrence. 1979. Methods in yeast genetics: a laboratory manual. Cold Spring Harbor Laboratory, Cold Spring Harbor, N.Y.

49. Southern, E. M. 1975. Detection of specific sequences among DNA fragments separated by gel electrophoresis. J. Mol. Biol. 98:503–517.

50. Thevelein, J. M. 1984. Regulation of trehalose mobilization in fungi. Microbiol. Rev. 48:42–59.

51. Toh-e, A., H. Nakamura, and Y. Oshima. 1976. A gene controlling the synthesis of non specific alkaline phosphatase in *Saccharomyces cerevisiae*. Biochim. Biophys. Acta 428:182–192.

52. von Heijne, G. 1986. A new method for predicting signal sequence cleavage sites. Nucl. Acids Res. 14:4683–4690.

53. Werner-Washburne, M., E. Braun, G. C. Johnston, and R. A. Singer. 1993. Stationary phase in the yeast *Saccharomyces cerevisiae*. Microbiol. Rev. 57:383–401.

54. Wickerham, L. J. 1946. A critical evaluation of the nitrogen assimilation tests commonly used in the classification of yeasts. J. Bacteriol. 52:293–301.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid of at least 20 base pairs which hybridizes with a nucleic acid consisting of nucleotides 10 to 408 of SEQ ID NO:1 at 50° C. in SSC (0.9 M saline/0.09 M sodium citrate) and remaining bound when subject to washing at 55° C. with SSC, wherein said isolated nucleic acid regulates the transcription of a gene joined in cis to said isolated nucleic acid.

2. An isolated nucleic acid consisting of the nucleic acid sequence of FIG. 1 (SEQ ID NO:1) between positions −360 and +39, wherein said isolated nucleic acid regulates the transcription of a gene joined in cis to said isolated nucleic acid.

3. A nucleic acid vector comprising a first isolated nucleic acid according to claim 1 or 2 joined in cis to a second nucleic acid encoding a protein, wherein said first isolated nucleic acid regulates the transcription of said second nucleic acid.

4. A eukaryotic cell comprising the nucleic acid vector of claim 3.

5. A eukaryotic cell according to claim 4, wherein said first isolated nucleic acid regulates the transcription of said second nucleic acid in response to a change in availability of a nutrient to said cell.

6. A eukaryotic cell according to claim 5, wherein said nutrient is glucose, ethanol, phosphate or a nitrogen source.

7. A eukaryotic cell according to claim 4, wherein said eukaryotic cell is a fungal cell.

8. A eukaryotic cell according to claim 4, wherein said eukaryotic cell is a yeast cell.

9. A method of producing recombinant protein, said method comprising the steps of:

forming a cell culture by contacting a eukaryotic cell according to claim 5 with a medium comprising said nutrient;

incubating said culture under conditions whereby said protein is expressed; and isolating said protein from said culture.

10. A method according to claim 9, wherein said protein is heterologous to said eukaryotic cell.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 2165 base pairs ( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 370..1434

( x i ) SEQUENCE DESCRIPTION: SEQ ID NO:1:

```
ATTCGTACTC TATTGCATCT TCAAAGTCCG AAGAATCTCA GTAGGGAGTG AAGCCGGCTT        60

CTCGATGCTA CACTTCTCGA TGCTACAGTT CAACATCGAT ACTTTGAAGA AAGAAAGCGC       120

CTATTATATC TCTTTTACCC TATTAGTAAT AATTAGGAAA AAGGGAGAAA AAAGTACCTC       180

ACTAAAAAAA CCATCATCTC TGAAATATAA AAAGCTTGAT AGAGGGTGAC ATTTGCTAGA       240

ACTTCTGCTG TGTTCTCTTG GGTTATTGCT CTTATTGAAT ATCCCTTCTA TTTCTTTCTT       300

GCTTGTAAAA AATCAGCTCA AAAACATCT ACAGGATTAA TCGTCAGTTA AGTAATACAG        360

TAATAGAAA ATG AAG TTC CAA GTT GTT TTA TCT GCC CTT TTG GCA TGT           408
           Met Lys Phe Gln Val Val Leu Ser Ala Leu Leu Ala Cys
             1               5                  10

TCA TCT GCC GTC GTC GCA AGC CCA ATC GAA AAC CTA TTC AAA TAC AGG         456
Ser Ser Ala Val Val Ala Ser Pro Ile Glu Asn Leu Phe Lys Tyr Arg
         15              20                  25

GCT GTT AAG GCA TCT CAC AGT AAG AAT ATC AAC TCC ACT TTG CCG GCA         504
Ala Val Lys Ala Ser His Ser Lys Asn Ile Asn Ser Thr Leu Pro Ala
30              35                  40                      45

TGG GAT GGG TCT AAC TCT AGC AAT GTT ACC TAC GCT AAT GGA ACA AAC         552
Trp Asp Gly Ser Asn Ser Ser Asn Val Thr Tyr Ala Asn Gly Thr Asn
                50                  55                  60

AGT ACT ACC AAT ACT ACT ACT GCC GAA AGC AGT CAA TTA CAA ATC ATT         600
Ser Thr Thr Asn Thr Thr Thr Ala Glu Ser Ser Gln Leu Gln Ile Ile
                65                  70                  75

GTA AGA GGT GGT CAA GTA CCA ATC ACC AAC AGT TCT TTG ACC CAC ACA         648
Val Arg Gly Gly Gln Val Pro Ile Thr Asn Ser Ser Leu Thr His Thr
            80                  85                  90

AAC TAC ACC AGA TTA TTC AAC AGT TCT TCT GCT TTG AAC ATT ACC GAA         696
Asn Tyr Thr Arg Leu Phe Asn Ser Ser Ser Ala Leu Asn Ile Thr Glu
        95                  100                 105

TTG TAC AAT GTT GCC CGT GTT GTT AAC GAA ACG ATC CAA GAT AAG TCA         744
Leu Tyr Asn Val Ala Arg Val Val Asn Glu Thr Ile Gln Asp Lys Ser
110                 115                 120                 125

TCC GCC GGT GCC GTT GTT GTT GCC AAC GCC AAA TCT TTG GAA GCT GTC         792
Ser Ala Gly Ala Val Val Val Ala Asn Ala Lys Ser Leu Glu Ala Val
                130                 135                 140

TCA TTC TTC TTC TCT ATC ATT TTT GAC ACC GAA AAG CCT ATT GTT GTC         840
Ser Phe Phe Phe Ser Ile Ile Phe Asp Thr Glu Lys Pro Ile Val Val
            145                 150                 155

ACT GAA GAT TCC GCT TAT GCC ATT CCA GTC GCT AAC AAT AAG AAC GCT         888
Thr Glu Asp Ser Ala Tyr Ala Ile Pro Val Ala Asn Asn Lys Asn Ala
        160                 165                 170

ACC AAA CGT GGT GTC TTG TCC GTC ACT TCT GAC AAA TTA GTG TAC TCC         936
Thr Lys Arg Gly Val Leu Ser Val Thr Ser Asp Lys Leu Val Tyr Ser
    175                 180                 185

GGT GTC TTC ACT CCA CCT ACT GCT TGT TCT TAC GGT GCT GGT TTG CCT         984
Gly Val Phe Thr Pro Pro Thr Ala Cys Ser Tyr Gly Ala Gly Leu Pro
190                 195                 200                 205

GTT GCT ATC GTT GAT GAC CAA GAC GAA GTT AAA TGG TTC TTC GAT GCT        1032
Val Ala Ile Val Asp Asp Gln Asp Glu Val Lys Trp Phe Phe Asp Ala
                210                 215                 220
```

-continued

| | | | | | | | | | | | | | | | | |
|---|---|---|---|---|---|---|---|---|---|---|---|---|---|---|---|---|
| TCT | AAG | CCA | ACT | TTA | ATC | TCT | TCT | GAC | TCG | ATT | ATC | AGA | AAG | GAA | TAC | 1080 |
| Ser | Lys | Pro | Thr | Leu | Ile | Ser | Ser | Asp | Ser | Ile | Ile | Arg | Lys | Glu | Tyr | |
| | | | 225 | | | | | 230 | | | | | 235 | | | |
| AGT | AAC | TTC | ACT | ACT | CCT | TAT | GGT | CTA | TTA | GAA | AAC | GGT | GTT | CCA | ATT | 1128 |
| Ser | Asn | Phe | Thr | Thr | Pro | Tyr | Gly | Leu | Leu | Glu | Asn | Gly | Val | Pro | Ile | |
| | | 240 | | | | | 245 | | | | | 250 | | | | |
| GTT | CCA | ATT | GTC | TAT | GAC | GGT | GGT | TAC | TCT | TCC | AGT | TTG | ATT | GAC | TCC | 1176 |
| Val | Pro | Ile | Val | Tyr | Asp | Gly | Gly | Tyr | Ser | Ser | Ser | Leu | Ile | Asp | Ser | |
| | | 255 | | | | | 260 | | | | | 265 | | | | |
| TTG | AGT | TCT | GCC | GTT | CAA | GGT | TTG | GTT | GTT | GTT | TCT | TCT | GGT | TCT | ACC | 1224 |
| Leu | Ser | Ser | Ala | Val | Gln | Gly | Leu | Val | Val | Val | Ser | Ser | Gly | Ser | Thr | |
| 270 | | | | | 275 | | | | | 280 | | | | | 285 | |
| AAC | TCA | ACC | TCA | TCT | ACT | ATT | GAA | AGC | ACT | GAA | ATC | CCA | GTC | GTA | TAT | 1272 |
| Asn | Ser | Thr | Ser | Ser | Thr | Ile | Glu | Ser | Thr | Glu | Ile | Pro | Val | Val | Tyr | |
| | | | | 290 | | | | | 295 | | | | | 300 | | |
| GCT | CAA | GCT | AAC | ACT | CCA | TTA | AAC | TTT | ATT | GAC | AAC | AAA | GAT | GTT | CCA | 1320 |
| Ala | Gln | Ala | Asn | Thr | Pro | Leu | Asn | Phe | Ile | Asp | Asn | Lys | Asp | Val | Pro | |
| | | | | 305 | | | | | 310 | | | | | 315 | | |
| AAG | AAC | GCT | GTG | GGT | GCT | GGT | TAC | CTA | TCC | CCA | ATT | AAG | GCC | CAA | ATC | 1368 |
| Lys | Asn | Ala | Val | Gly | Ala | Gly | Tyr | Leu | Ser | Pro | Ile | Lys | Ala | Gln | Ile | |
| | | | 320 | | | | | 325 | | | | | 330 | | | |
| TTG | TTG | TCC | ATT | GCT | GCC | GTT | AAT | GGT | GTC | ACC | TCC | AAG | TCC | GCT | CTG | 1416 |
| Leu | Leu | Ser | Ile | Ala | Ala | Val | Asn | Gly | Val | Thr | Ser | Lys | Ser | Ala | Leu | |
| | | 335 | | | | | 340 | | | | | 345 | | | | |
| GAA | AGC | ATT | TTC | CCA | TGAACTGATA | GATATTAAAT | CTAGCGAAGC | ATAGAGATTC | | | | | | | | 1471 |
| Glu | Ser | Ile | Phe | Pro | | | | | | | | | | | | |
| 350 | | | | | 355 | | | | | | | | | | | |

| | | | | |
|---|---|---|---|---|
| TTTTTTTACC | AGTCATCATA | ACCATTATTT | TACAAAATTT | CCACGCAACA GCTTTTATTT | 1531 |
| TCGTTCGTAA | TAGGAACCAT | ACTTCCCATT | AAAGCAGTAT | GATTGTTTTA TACACCTTTT | 1591 |
| TATTGTTATT | TAAGACATAC | CCCAAATAAT | TAATTAATTA | ATTGATGAAA GAATCATATA | 1651 |
| AATTCTTGGC | CATACATATT | TTTTTATTAT | CTTTTGCTAC | ATTGACCATA GGTGAATATC | 1711 |
| TTCCCGGGGT | GACACTCCAC | TGAAGTGGGA | AAAAAAGAAA | AGTTTAAAA CATTGCTCAC | 1771 |
| CTTAAGTCTC | GAAGGTCTAG | CATTCACTAC | CTGTAAGTGT | CAAGACCCCA CAGGTATACA | 1831 |
| TGATACAATA | AAGAAACAAT | GTCCGTATAA | TTGTATACAT | TTTACTACAG ATAAGGGATC | 1891 |
| TCACCCCCTT | CTTTTGTGTC | TAAGTGAAAT | CTTCTGATAT | ATTTAGTGTT TTATAGCGTC | 1951 |
| CATGTTTTAA | ACTAGAACGG | CAAAATAGTA | GTTGTTGTAA | ACGCTTATTT TCGAGACATC | 2011 |
| AGGTAAAAAG | ATAGTTAAAT | CTTACAATCA | ATGCATGTAG | TGAGTGGCGT TTATCAATAG | 2071 |
| TTTTTAACAA | TTCCATTTTT | GAAAGAAGCC | CACAACAACC | CTAGTAGTTC GTTATATACG | 2131 |
| TTATGATGGT | CAAGTGTCAC | AGTACGGAAA | GCTT | | 2165 |

( 2 ) INFORMATION FOR SEQ ID NO:2:

( i ) SEQUENCE CHARACTERISTICS:
        ( A ) LENGTH: 354 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Lys | Phe | Gln | Val | Val | Leu | Ser | Ala | Leu | Leu | Ala | Cys | Ser | Ser | Ala |
| 1 | | | | 5 | | | | | 10 | | | | | 15 | |
| Val | Val | Ala | Ser | Pro | Ile | Glu | Asn | Leu | Phe | Lys | Tyr | Arg | Ala | Val | Lys |
| | | | 20 | | | | | 25 | | | | | 30 | | |
| Ala | Ser | His | Ser | Lys | Asn | Ile | Asn | Ser | Thr | Leu | Pro | Ala | Trp | Asp | Gly |
| | | | 35 | | | | | 40 | | | | | 45 | | |

| | | | | | | | | | | | | | | |
|---|---|---|---|---|---|---|---|---|---|---|---|---|---|---|
| Ser | Asn 50 | Ser | Ser | Asn | Val | Thr 55 | Tyr | Ala | Asn | Gly | Thr 60 | Asn | Ser | Thr | Thr |
| Asn 65 | Thr | Thr | Thr | Ala | Glu 70 | Ser | Ser | Gln | Leu | Gln 75 | Ile | Ile | Val | Arg | Gly 80 |
| Gly | Gln | Val | Pro | Ile 85 | Thr | Asn | Ser | Ser | Leu 90 | Thr | His | Thr | Asn | Tyr 95 | Thr |
| Arg | Leu | Phe | Asn 100 | Ser | Ser | Ser | Ala | Leu 105 | Asn | Ile | Thr | Glu | Leu 110 | Tyr | Asn |
| Val | Ala | Arg 115 | Val | Val | Asn | Glu | Thr 120 | Ile | Gln | Asp | Lys | Ser 125 | Ser | Ala | Gly |
| Ala | Val 130 | Val | Val | Ala | Asn | Ala 135 | Lys | Ser | Leu | Glu | Ala 140 | Val | Ser | Phe | Phe |
| Phe 145 | Ser | Ile | Ile | Phe | Asp 150 | Thr | Glu | Lys | Pro | Ile 155 | Val | Val | Thr | Glu | Asp 160 |
| Ser | Ala | Tyr | Ala | Ile 165 | Pro | Val | Ala | Asn | Asn 170 | Lys | Asn | Ala | Thr | Lys 175 | Arg |
| Gly | Val | Leu | Ser 180 | Val | Thr | Ser | Asp | Lys 185 | Leu | Val | Tyr | Ser | Gly 190 | Val | Phe |
| Thr | Pro | Pro 195 | Thr | Ala | Cys | Ser | Tyr 200 | Gly | Ala | Gly | Leu | Pro 205 | Val | Ala | Ile |
| Val | Asp 210 | Asp | Gln | Asp | Glu | Val 215 | Lys | Trp | Phe | Phe | Asp 220 | Ala | Ser | Lys | Pro |
| Thr 225 | Leu | Ile | Ser | Ser | Asp 230 | Ser | Ile | Ile | Arg | Lys 235 | Glu | Tyr | Ser | Asn | Phe 240 |
| Thr | Thr | Pro | Tyr | Gly 245 | Leu | Leu | Glu | Asn | Gly 250 | Val | Pro | Ile | Val | Pro 255 | Ile |
| Val | Tyr | Asp | Gly 260 | Gly | Tyr | Ser | Ser | Ser 265 | Leu | Ile | Asp | Ser | Leu 270 | Ser | Ser |
| Ala | Val | Gln 275 | Gly | Leu | Val | Val | Val 280 | Ser | Ser | Gly | Ser | Thr 285 | Asn | Ser | Thr |
| Ser | Ser 290 | Thr | Ile | Glu | Ser | Thr 295 | Glu | Ile | Pro | Val | Val 300 | Tyr | Ala | Gln | Ala |
| Asn 305 | Thr | Pro | Leu | Asn | Phe 310 | Ile | Asp | Asn | Lys | Asp 315 | Val | Pro | Lys | Asn | Ala 320 |
| Val | Gly | Ala | Gly | Tyr 325 | Leu | Ser | Pro | Ile | Lys 330 | Ala | Gln | Ile | Leu | Leu 335 | Ser |
| Ile | Ala | Ala | Val 340 | Asn | Gly | Val | Thr | Ser 345 | Lys | Ser | Ala | Leu | Glu 350 | Ser | Ile |
| Phe | Pro | | | | | | | | | | | | | | |